US009404924B2

(12) United States Patent
Love et al.

(10) Patent No.: US 9,404,924 B2
(45) Date of Patent: Aug. 2, 2016

(54) METHOD OF PERFORMING ONE-STEP, SINGLE CELL RT-PCR

(75) Inventors: J. Christopher Love, Somerville, MA (US); Yuan Gong, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/911,642

(22) Filed: Oct. 25, 2010

(65) Prior Publication Data

US 2011/0111981 A1 May 12, 2011

Related U.S. Application Data

(63) Continuation-in-part of application No. PCT/US2009/066876, filed on Dec. 4, 2009.

(60) Provisional application No. 61/254,505, filed on Oct. 23, 2009, provisional application No. 61/120,033, filed on Dec. 4, 2008.

(51) Int. Cl.
*C12Q 1/68* (2006.01)
*C12P 19/34* (2006.01)
*G01N 33/569* (2006.01)
*C12Q 1/70* (2006.01)

(52) U.S. Cl.
CPC .......... *G01N 33/56983* (2013.01); *C12Q 1/703* (2013.01); *C12Q 2600/136* (2013.01); *C12Q 2600/158* (2013.01)

(58) Field of Classification Search
CPC ............. C12Q 1/703; C12Q 2600/136; C12Q 2600/0158; G01N 33/56983
See application file for complete search history.

(56) References Cited

U.S. PATENT DOCUMENTS

| 4,729,949 | A | 3/1988 | Weinreb et al. |
| 6,210,910 | B1 | 4/2001 | Walt et al. |
| 6,377,721 | B1 | 4/2002 | Walt et al. |
| 6,410,252 | B1 | 6/2002 | Lehmann et al. |
| 7,776,553 | B2 | 8/2010 | Love et al. |
| 9,244,080 | B2 | 1/2016 | Love et al. |
| 2010/0255471 | A1* | 10/2010 | Clarke et al. ............ 435/6 |
| 2011/0111981 | A1 | 5/2011 | Love et al. |

FOREIGN PATENT DOCUMENTS

| JP | H08-259598 A | 10/1996 |
| JP | 2003-531377 A | 10/2003 |
| JP | 2004-528546 A | 9/2004 |
| JP | 2009-520029 A | 5/2009 |
| WO | WO-01/79843 A2 | 10/2001 |
| WO | WO-02/073195 A2 | 9/2002 |
| WO | WO-02/078844 A1 | 10/2002 |
| WO | WO 03/035824 A1 | 5/2003 |
| WO | WO 2007/035633 A2 | 3/2007 |
| WO | WO-2007/075605 A2 | 7/2007 |
| WO | WO 2008135196 A1 * | 11/2008 |
| WO | WO-2009/145925 A1 | 12/2009 |
| WO | WO-2010/085275 A1 | 7/2010 |
| WO | WO-2010/096652 A1 | 8/2010 |

OTHER PUBLICATIONS

Warran et al., "Transcription factor profiling in individual hematopoietic progenitors by digital RT-PCR," PNAS, Nov. 2006, vol. 103, No. 47, pp. 17807-17812.*
Sasuga et al., "Single-Cell Chemical Lysis Method for Analyses of Intracellular Molecules Using an Array of Picoliter-Scale Microwells," Analytical Chemistry, 2008, vol. 80, pp. 9141-9149.*
Khattri et al., "An essential role for Scurfin in CD4+ CD25+ T regulatory cells," Nature Immunology, 2003, vol. 4, No. 4, pp. 337-342.*
Schutten et al., "Development of a real-time quantitative RT-PCR for the detection of HIV-2 RNA in plasma," Journal of Virological Methods, 2000, vol. 88, pp. 81-87.*
Beer et al., "On-Chip Single-Copy Real-Time Reverse-Transcription PCR in Isolated Picoliter Droplets," Analytical Chemistry, 2008, vol. 80, pp. 1854-1858.*
Kumaresan et al., "High-Throughput Single Copy DNA Amplification and Cell Analysis in Engineered Nanoliter Droplets," Analytical Chemistry, Apr. 2008, vol. 80, pp. 3522-3529.*
International Search Report, PCT/US2009/066876, Mailed Jul. 20, 2010, (5 pages).
Written Opinion for PCT/US2009/066876, Mailed Jul. 20, 2010, (5 pages).
Bradshaw et al., Concurrent detection of secreted products from human lymphocytes by microengraving: Cytokines and antigen-reactive antibodies, *Clinical Immunology*, 129(1):10-18 (2008).
Love J C et al., "A microengraving method for rapid selection of single cells producing antigen-specific antibodies" *Nature BioTechnology*, 24(6): 703-707 (2006).
Kent et al., "Enumeration and Phenotype of Autoreactive B Cells in Pancreatic Draining Lymph Nodes from Types 1 Diabetes Subjects", *Clinical Immunology*, 131(1): S19 (2009).
Harriman et al., "Antibody discovery via multiplexed single cell characterization", *Journal of Immunological Methods*, 341:135-145 (2009).
Abbas et al., Cellular and Molecular Immunology, 2nd Ed.: 92-93 (1994).
Alberts, B. et al., Looking at the Structure of Cells in the Microscope, Molecular Biology of the Cell, 4:551 (2002).
Chen, H.J.H. et al., A Novel Micro-Well Array Chip for Liquid Phase Biomaterial Processing and Detection, Sensors and Actuators, 108:193-200 (2003).
Clark et al., Regulation of Human B-Cell Activation and Adhesion, Annual Review Immunology, 9: 97-127 (1991).

(Continued)

*Primary Examiner* — Young J Kim
(74) *Attorney, Agent, or Firm* — Choate, Hall & Stewart, LLP

(57) ABSTRACT

The invention provides methods for detecting virus production, determining frequency and identity of HIV reservoirs, or evaluating gene expression on a single-cell basis using microengraving and RT-PCR.

18 Claims, 9 Drawing Sheets

(56) References Cited

OTHER PUBLICATIONS

Communication pursuant to Article 94(3) EPC for EP09799214.3, 4 pages (Nov. 5, 2013).
First Office Action for CN200980156181.4, 11 pages (Jul. 5, 2013).
Haining, W.N., Travels in time: Assessing the functional complexity of T cells, PNAS, 109(5):1359-1360 (2012).
Muraguchi et al., Method for Cloning Antigen-Specific Lymphocyte Antigen Receptor Gene, English Translation of Japanese Patent Application No. 2002-346728, (filed Nov. 29, 2002).
Muraguchi et al., Microwell Array Chip for Detecting Antigen-Specific Lymphocytes and Method for Detecting Antigen-Specific Lymphocytes, English Translation of Japanese Patent Application No. 2002-331031, (filed Nov. 14, 2002).
Notice of Reasons for Rejection for JP2011539763, 2 pages (Nov. 13, 2013).
Official Action for IL213206, 5 pages (Jul. 22, 2013).
Opposition against European Patent No. 1566635, 28 pages (Sep. 7, 2012).
Ostuni, E. et al., Selective Deposition of Proteins and Cells in Arrays of Microwells, Langmuir, 17:2828-2834 (2001).
Reply to Opposition against European Patent No. 1566635, 25 pages (Apr. 29, 2013).
Steenbakkers, P.G. et al., A new approach to the generation of human or murine antibody producing hybridomas, J. Immunol. Method, 152:(1)69-77 (1992).
Van Duin, J. and Tsareva, N., Single-Stranded RNA Phages, The Bacteriophages, 2(15):175-196 (2006).
Warren, L., Single-Cell Gene-Expression Analysis by Quanitative RT-PCR, California Institute of Technology, 1-225 (2008).
Written Opinion for SG 201104033-4, 8 pages (Sep. 24, 2012).
Bailey, J.R. et al., Residual human immunodeficiency virus type 1 viremia in some patients on antiretroviral therapy is dominated by a small number of invariant clones rarely found in circulating CD4+ T cells, J. Virol., 80(13):6441-57 (2006).
Beer, N.R. et al., On-chip, real-time, single-copy polymerase chain reaction in picoliter droplets, Anal. Chem., 79(22):8471-5 (2007).
Bengtsson, M. et al., Quantification of mRNA in single cells and modelling of RT-qPCR induced noise, BMC Mol. Biol., 9:63 (2008).
Carpenter, A.E. et al., CellProfiler: image analysis software for identifying and quantifying cell phenotypes, Genome Biol. 7(10):R100 (2006).
Chen, C. et al. Real-time quantification of microRNAs by stem-loop RT-PCR, Nucleic Acids Res., 33(20):e179 (2005).
Chun, T.W. et al., In vivo fate of HIV-1-infected T cells: quantitative analysis of the transition to stable latency, Nat. Med., 1(12):1284-90 (1995).
Chun, T.W. et al., Presence of an inducible HIV-1 latent reservoir during highly active antiretroviral therapy, Proc. Natl. Acad. Sci. U S A, 94(24):13193-7 (1997).
Chun, T.W. et al., Quantification of latent tissue reservoirs and total body viral load in HIV-1 infection, Nature, 387(6629):183-8 (1997).
Deeks, S.G. et al., Virologic and immunologic consequences of discontinuing combination antiretroviral-drug therapy in HIV-infected patients with detectable viremia, N. Engl. J. Med., 344(7):472-80 (2001).
Dicarlo, D. and Lee, L.P., Dynamic single-cell analysis for quantitative biology, Anal. Chem., 78(23):7918-25 (2006).
Diehl, F. et al., BEAMing: single-molecule PCR on microparticles in water-in-oil emulsions, Nat. Methods., 3(7):551-9 (2006).
Embleton, M.J. et al., In-cell PCR from mRNA: amplifying and linking the rearranged immunoglobulin heavy and light chain V-genes within single cells, Nucleic Acids Res., 20(15):3831-7 (1992).
Embretson, J. et al., Analysis of human immunodeficiency virus-infected tissues by amplification and in situ hybridization reveals latent and permissive infections at single-cell resolution, Proc. Natl. Acad. Sci. U S A., 90(1):357-61 (1993).
Engvall, E. and Perlmann, P., 3. Quantitation of specific antibodies by enzyme-labeled anti-immunoglobulin in antigen-coated tubes, J. Immunol., 109(1):129-35 (1972).

Finzi D. et al., Latent infection of CD4+ T cells provides a mechanism for lifelong persistence of HIV-1, even in patients on effective combination therapy, Nat. Med., 5(5):512-7 (1999).
Finzi, D. et al., Identification of a reservoir for HIV-1 in patients on highly active antiretroviral therapy, Science, 278(5341):1295-300 (1997).
Han, Q. et al., Multidimensional analysis of the frequencies and rates of cytokine secretion from single cells by quantitative microengraving, Lab Chip, 10(11):1391-400 (2010).
Han, Y. et al., Experimental approaches to the study of HIV-1 latency, Nat. Rev. Microbiol., 5(2):95-106 (2007).
Han, Y. et al., Resting CD4+ T cells from human immunodeficiency virus type 1 (HIV-1)-infected individuals carry integrated HIV-1 genomes within actively transcribed host genes, J. Virol., 78(12):6122-33 (2004).
Hermankova, M. et al., Analysis of human immunodeficiency virus type 1 gene expression in latently infected resting CD4+ T lymphocytes in vivo, J. Virol., 77(13):7383-92 (2003).
Holland, P.M. et al., Detection of specific polymerase chain reaction product by utilizing the 5'-3' exonuclease activity of Thermus aquaticus DNA polymerase, Proc. Natl. Acad. Sci. U S A., 88(16):7276-80 (1991).
Kiss, M.M. et al., High-throughput quantitative polymerase chain reaction in picoliter droplets, Anal. Chem., 80(23):8975-81 (2008).
Lassen, K.G. et al., Analysis of human immunodeficiency virus type 1 transcriptional elongation in resting CD4+ T cells in vivo, J. Virol., 78(17):9105-14 (2004).
Lassen, K.G. et al., Nuclear retention of multiply spliced HIV-1 RNA in resting CD4+ T cells, PLoS Pathog., 2(7):e68 (2006).
Leamon, J.H. et al., A massively parallel PicoTiterPlate based platform for discrete picoliter-scale polymerase chain reactions, Electrophoresis, 24(21):3769-77 (2003).
Lindström, S. et al., PCR amplification and genetic analysis in a microwell cell culturing chip, Lab Chip, 9(24):3465-71 (2009).
Liss, B., Improved quantitative real-time RT-PCR for expression profiling of individual cells, Nucleic Acids Res., 30(17):e89 (2002).
Malnati, M.S. et al., A universal real-time PCR assay for the quantification of group-M HIV-1 proviral load, Nat. Protoc., 3(7):1240-8 (2008).
Marcus, J.S. et al., Microfluidic single-cell mRNA isolation and analysis, Anal. Chem., 78(9):3084-9 (2006).
Marcus, J.S. et al., Parallel picoliter rt-PCR assays using microfluidics, Anal. Chem., 78(3):956-8 (2006).
Margulies, M. et al., Genome sequencing in microfabricated high-density picolitre reactors, Nature, 437(7057):376-80 (2005).
Mazutis, L. et al., Droplet-based microfluidic systems for high-throughput single DNA molecule isothermal amplification and analysis, Anal. Chem., 81(12):4813-21 (2009).
Meijer, P.J. et al., Isolation of human antibody repertoires with preservation of the natural heavy and light chain pairing, J. Mol. Biol., 358(3):764-72 (2006).
Monie, D. et al., A novel assay allows genotyping of the latent reservoir for human immunodeficiency virus type 1 in the resting CD4+ T cells of viremic patients, J. Virol., 79(8):5185-202 (2005).
Nagai, H. et al., Development of a microchamber array for picoliter PCR, Anal. Chem., 73(5):1043-7 (2001).
No Author Listed, Executive summary, 2008 Report on the global AIDS epidemic, Joint United Nations Programme on HIV/AIDS (UNAIDS), 36 pages (2008).
Ogunniyi, A.O. et al., Screening individual hybridomas by microengraving to discover monoclonal antibodies, Nat. Protoc., 4(5):767-82 (2009).
Persaud, D. et al., A stable latent reservoir for HIV-1 in resting CD4(+) T lymphocytes in infected children, J. Clin. Invest., 105(7):995-1003 (2000).
Schacker, T. et al., Rapid accumulation of human immunodeficiency virus (HIV) in lymphatic tissue reservoirs during acute and early HIV infection: implications for timing of antiretroviral therapy, J. Infect. Dis., 181(1):354-7 (2000).

(56) References Cited

OTHER PUBLICATIONS

Toriello, N.M. et al., Integrated microfluidic bioprocessor for single-cell gene expression analysis, Proc. Natl. Acad. Sci. U S A., 105(51):20173-8 (2008).

Wang, X. and Stollar, B.D., Human immunoglobulin variable region gene analysis by single cell RT-PCR, J. Immunol. Methods., 244(1-2):217-25 (2000).

Wong, J.K. et al., Recovery of replication-competent HIV despite prolonged suppression of plasma viremia, Science, 278(5341):1291-5 (1997).

Yamamura, S. et al., Single-cell microarray for analyzing cellular response, Anal. Chem., 77(24):8050-6 (2005).

Yu, X. et al., Neutralizing antibodies derived from the B cells of 1918 influenza pandemic survivors, Nature, 455(7212):532-6 (2008).

Zhang, K. et al., Sequencing genomes from single cells by polymerase cloning, Nat. Biotechnol., 24(6):680-6 (2006).

Zhou, Y et al., Kinetics of human immunodeficiency virus type 1 decay following entry into resting CD4+ T cells, J. Virol., 79(4):2199-210 (2005).

Zhu, T. et al., Evidence for human immunodeficiency virus type 1 replication in vivo in CD14(+) monocytes and its potential role as a source of virus in patients on highly active antiretroviral therapy, J. Virol., 76(2):707-16 (2002).

Han et al., Polyfunctional responses by human T cells result from sequential release of cytokines, Proceedings of the National Academy of Sciences, 105(5):1607-1612 (2012).

Warbrick, E.V. et al. Induced changes in total serum IgE concentration in the Brown Norway rat: potential for identification of chemical respiratory allergens, J. Appl. Toxicol., 22(1):1-11 (2002).

Alberts, B. et al., Molecular Biology of The Cell, Fourth Edition, Garland Science, p. 1445 (2002).

\* cited by examiner

METHOD OF PERFORMING ONE-STEP, SINGLE CELL RT-PCR

RELATED APPLICATIONS

This application claims priority to U.S. Ser. No. 61/254,505, filed Oct. 23, 2009, and is a continuation-in-part of PCT/US2009/066876, filed Dec. 4, 2009, which claims priority to 61/120,033, filed Dec. 4, 2008, the contents of each of which are incorporated herein by reference in their entirety.

STATEMENT AS TO FEDERALLY SPONSORED RESEARCH

This invention was funded in part by the U.S. Government under grant number 5T32GM008334-22, awarded by the National Institutes of Health. The Government has certain rights in the invention.

INCORPORATION-BY-REFERENCE OF SEQUENCE LISTING

The contents of the text file named "38172505seqlisting.txt", which was created on Dec. 6, 2010 and is 4 KB in size, are hereby incorporated by reference in their entirety.

FIELD OF THE INVENTION

The invention provides a method for profiling large numbers of single cells in microarrays.

BACKGROUND OF THE INVENTION

The relationship between the expression of certain genes and the subsequent functional activities of a cell is a central question in cell biology. The detection of transcribed genes often uses reverse transcription polymerase chain reaction (RT-PCR). RT-PCR is a variant of polymerase chain reaction (PCR), a laboratory technique commonly used in molecular biology to generate many copies of a deoxyribonucleic acid (DNA) sequence, a process termed "amplification." In RT-PCR, a ribonucleic acid (RNA) strand is first reverse transcribed into its DNA complement (complementary DNA, or cDNA) using the enzyme reverse transcriptase. The resulting cDNA is subsequently amplified using traditional PCR. RT-PCR utilizes a pair of primers, which are complementary to a defined sequence on each of the two strands of the cDNA. These primers are then extended by a DNA polymerase and a copy of the strand is made after each PCR cycle, leading to exponential amplification.

SUMMARY OF THE INVENTION

Described herein is a one-step process for detecting the expression of specific genes in thousands of single cells in parallel. The methods enable an integrated single-cell analysis of both the expression of specific genes and secretion of the corresponding translated protein from each cell (e.g., by immunofluoresence or genetic sequencing). For example, the methods are useful for detection and functional phenotyping of cells infected with retroviruses or intracellular pathogens, and the amplification of specific genes from many cells in parallel for downstream genetic analysis by sequencing.

The invention provides a method of performing one-step, single-cell, RT-PCR. First, cells are deposited onto a microdevice. In some cases, the cells are a population of cells obtained from a mammal, e.g., cells from blood or a tissue. The mammal can be, e.g., any mammal, e.g., a human, a primate, a mouse, a rat, a dog, a cat, a cow, a horse, or a pig. In a preferred embodiment, the mammal is a human. In another example, the cells are from a library of cells, e.g., a purchased library of cells. Suitable cells include immune cells (e.g., T cells, macrophages, monocytes, or dendritic cells), antibody-producing cells (e.g., B cells), hybridoma cells, stem cells, cancer cells, or other cells from the blood or a tissue. T cells or T lymphocytes belong to a group of white blood cells known as lymphocytes, and play a central role in cell-mediated immunity. Examples of T cells include T helper ($T_H$) cells (e.g., $T_H1$, $T_H2$, $T_H3$, $T_H17$, or $T_{FH}$), cytotoxic T cells (CTLs), memory T cells, regulatory T cells, natural killer T cells (NKT cells), and gamma delta T cells.

The cells are deposited onto a microdevice that contains wells that spatially separate the cells at fewer than 5 cells, e.g., fewer than 4 cells, fewer than 3 cells, fewer than 2 cells, e.g., a single cell per well. The cells are in suspension in a volume of media. The wells are between about 10 and 100 µm in diameter; between about 25 and 75 µm; between about 45 and 55 µm, e.g., about 50 µm in diameter. Alternatively, the wells are between about 10 and 50 µm; between about 20 and 40 µm; between about 25 and 35 µm, e.g., about 30 µm in diameter. The reaction is performed in a volume less than 1 µL, e.g., less than 1 nL or less than 500 pL. For example, the reaction is performed in a volume of between about 10 pL and 1,000 pL; between about 50 pL and 500 pL; or between about 100 pL and 200 pL, e.g., about 125 pL. Alternatively, the reaction is performed in a volume of between about 1 pL and 500 pL; between about 10 pL and 100 pL; between about 15 pL and 50 pL; between about 20 pL and 40 pL; between about 25 pL and 30 pL, e.g, about 27 pL.

The cell in suspension (or a volume of tissue culture media bathing the cell) is contacted with one or more reagents to perform RT-PCR, and the wells are sealed to constrain single cells in individual volumes for lysis and RT-PCR. Preferably, the wells are sealed to a glass, silicon, or plastic slide. In some cases, the following RT-PCR reagents are introduced into the well: a lysis reagent, a reverse transcription reagent, and a complementary deoxyribonucleic acid (cDNA) amplification reagent. For example, suitable lysis reagents include detergent (NP-40), methanol, and water. Reverse transcriptase is introduced into the wells to begin reverse transcription of mRNA into cDNA. Taq polymerase, a thermostable DNA polymerase, is also introduced to catalyze the PCR amplification of cDNA. Gene-specific TAQMAN® probe and primers are also added to the wells. TAQMAN® probes are of a fluorophore covalently attached to the 5'-end of the oligonucleotide probe and a quencher at the 3'-end for real-time PCR quantification. Alternatively, fluorescent dyes that intercalcate into DNA, e.g., Sybr Green, are used to detect PCR amplification. In another aspect, deoxynucleoside triphosphates (dNTPs), the building blocks from which the DNA polymerases synthesize new DNA strands are added to the well. In some instances, the dNTPs are fluorescently labeled or tagged for detection. Optionally, a ribonuclease (RNase) inhibitor, such as SUPERASE IN™ RNase inhibitor is added to the well. In some cases, the wells and cells are stained with a reference dye 5-carboxy-X-rhodamine (ROX).

The invention also provides methods of performing solution-phase cell screening. Specifically, microengraving is used to identify which cells initially are active virus producers by detecting viral activity. For example, viral activity is identified by detecting a viral peptide (e.g., p24, env, gp120, gp41, or p17), a viral fragment, or a whole virion. Viral fragments or whole virions are detected utilizing virus-specific antibodies in a standard virus capture assay, e.g., a sandwich assay. Then, the cells are stimulated in the device and allowed to produce new virus followed by a second printing step, wherein microengraving is used to identify which cells are active producers after stimulation by detecting viral peptides, viral fragments, or whole virions.

First, cells are cultured in the presence of an anti-retroviral compound. In some cases, the cells are a population of cells obtained from a mammal, e.g., cells from blood or a tissue. The mammal can be, e.g., any mammal, e.g., a human, a primate, a mouse, a rat, a dog, a cat, a cow, a horse, or a pig. In a preferred embodiment, the mammal is a human. In some cases, the cells are from a library of cells, e.g., a purchased library of cells. Suitable cells include immune cells (e.g., T cells, macrophages, monocytes, or dendritic cells), antibody-producing cells (e.g., B cells), hybridoma cells, stem cells, cancer cells, or other cells from the blood or a tissue. T cells or T lymphocytes belong to a group of white blood cells known as lymphocytes, and play a central role in cell-mediated immunity. Examples of T cells include T helper ($T_H$) cells (e.g., $T_H1$, $T_H2$, $T_H3$, $T_H17$, or $T_{FH}$), cytotoxic T cells (CTLs), memory T cells, regulatory T cells, natural killer T cells (NKT cells), and gamma delta T cells. Suitable anti-retroviral compounds include nucleoside and nucleotide reverse transcriptase inhibitors (NRTI; e.g., zidovudine), which inhibit reverse transcription by being incorporated into the newly synthesized viral deoxyribonucleic acid (DNA) and preventing its further elongation. Non-nucleoside reverse transcriptase inhibitors (NNRTI; e.g, efavirenz) inhibit reverse transcriptase directly by binding to the enzyme and interfering with its function. Protease inhibitors (PIs; e.g., saquinavir) target viral assembly by inhibiting the activity of protease, an enzyme used by human immunodeficiency virus (HIV) to cleave nascent proteins for final assembly of new virons. Integrase inhibitors (e.g., raltegravir) inhibit the enzyme integrase, which is responsible for integration of viral DNA into the DNA of the infected cell. Entry inhibitors (or fusion inhibitors; e.g., maraviroc and enfuvirtide) interfere with binding, fusion and entry of HIV-1 to the host cell by blocking one of several targets. Finally, maturation inhibitors (e.g., alpha interferon) inhibit the last step in gag processing in which the viral capsid polyprotein is cleaved, thereby blocking the conversion of the polyprotein into the mature capsid protein (p24). Because these viral particles have a defective core, the virions released are mainly of non-infectious particles.

The cells are deposited onto a microdevice that contains wells that spatially separate the cells in at fewer than 5 cells, e.g., fewer than 4 cells, fewer than 3 cells, fewer than 2 cells, e.g., a single cell per well. The cells are in solution or in suspension in a volume of media. The wells are between about 10 and 100 µm in diameter; between about 25 and 75 µm; between about 45 and 55 µm, e.g., about 50 µm in diameter. Alternatively, the wells are between about 10 and 50 µm; between about 20 and 40 µm; between about 25 and 35 µm, e.g., about 30 µm in diameter. The reaction is performed in a volume less than 1 µL, e.g., less than 1 nL or less than 500 pL. For example, the reaction is performed in a volume of between about 10 pL and 1,000 pL; between about 50 pL and 500 pL; or between about 100 pL and 200 pL, e.g., about 125 pL. Alternatively, the reaction is performed in a volume of between about 1 pL and 500 pL; between about 10 pL and 100 pL; between about 15 pL and 50 pL; between about 20 pL and 40 pL; between about 25 pL and 30 pL, e.g, about 27 pL. The suspension or solution is contacted with at least one optical signal substrate, each indicative of a desired viral activity. Cells are identified as virus-producing cells if a desired viral activity is present. Cells are identified as non-virus-producing cells if a desired viral activity is absent. Viral activity is identified by detecting a viral peptide, a viral fragment, or a whole virion.

In some cases, the "optical signal substrate" is a composite of one or more units, e.g., an antibody or other specific ligand or small molecule tag that is directly conjugated to a detectable marker. For example, in a two element reaction (e.g., X+Y catalyzed by a transferase enzyme), a first element, "Y", is captured by an antibody or other ligand that is immobilized on a surface such as a culture plate and the second element, "X", is detected with an optical substrate such as a fluorescently-tagged antibody. Optionally, the phenotype is evaluated by detecting changes over time in one or more optical signals generated by one or more optical signal substrates in the cells. The invention utilizes various chromogenic, fluorogenic, lumigenic and fluorescence resonance energy transfer (FRET) substrates to measure biological activity. Many donor/acceptor FRET pairs are commercially available. These include, but are not limited to: 5-carboxytetramethylrhodamine (TAMRA)/QSY-7 (diarylrhodamine derivative); Dansyl/Eosin; Tryptophan/Dansyl; Fluorescein/Texas Red (rhodamine); Naphthalene/Dansyl; Dansyl/octadecyl-rhodamine (ODR); boron-dipyrromethene (BODIPY)/BODIPY; Terbium/Thodamine; Dansyl/fluorescein isothiocyanate (FITC); Pyrere/Coumarin; 5-(2-iodoacetylaminoethyl)aminonaphthalene-1-sulfonic acid (IAEDANS)/IAFBPE/Cy5; and Europium/Cy5. Preferably, the optical signal is a fluorescence signal. In one aspect, activity is monitored in real-time or near-real-time in the microdevice on the basis of changes in the intensities of the fluorescent signal.

Optionally, the method further comprises stimulating the non-viral-producing cells in the microdevice. For example, the non-viral-producing cells are stimulated with phytohemagglutinin (PHA), gamma-irradiated virus-free peripheral blood mononuclear cells (PBMCs), or cross-linking anti-CD3 antibodies. Subsequently, the suspension or solution is contacted with at least one optical signal substrate, each indicative of a desired viral activity. Cells are identified as latently-infected viral cells if a desired viral activity is present. Viral activity is identified by detecting a viral peptide, a viral fragment, or a whole virion.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Suitable viruses include retroviruses, such as human immunodeficiency virus (HIV), human T cell leukemia virus (HTLV), herpes simplex virus (HSV) 1, HSV 2, or human endogenous retroviruses (hERV). Preferably, the HIV viral peptide is p24 (GenBank Accession Number AAL98907 (GI: 19773852), incorporated herein by reference), the core HIV capsid protein, or env (GenBank Accession Number AAB09538 (GI:1575476), incorporated herein by reference), the HIV envelope protein. Other HIV viral proteins that are useful in the methods described herein include gp120 (GenBank Accession Number AAF69493 (GI:7769646), incorporated herein by reference), gp41 (GenBank Accession Number AAA19156 (GI:468123), incorporated herein by reference), and p17 (GenBank Accession Number AAC17873 (GI:3169562), incorporated herein by reference).

In one aspect, the optical signal is a fluorescence signal. Optionally, the viral activity is monitored in real-time or near-real-time in the microdevice on the basis of changes in the intensities of said fluorescent signal. In one aspect, the cells are isolated by micromanipulation with a glass capillary. In another aspect, the method further comprises performing single cell reverse transcription polymerase chain reaction (RT-PCR) for group-specific antigen (gag) messenger ribonucleic acid (mRNA), polymerase (pol) mRNA, or envelope (env) mRNA in each cell. In one aspect, the method further comprises sequencing said HIV strain.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. For example, at least the following publications are incorporated herein by reference: WO 07/035,633, WO 09/145,925, WO 10/065,929, WO 10/085,275, and WO 10/096,652. In the case of conflict, the present specification, including definitions, will control. In addition, the materials, methods, and examples are illustrative only and not intended to be limiting.

DETAILED DESCRIPTION

Figure 1:
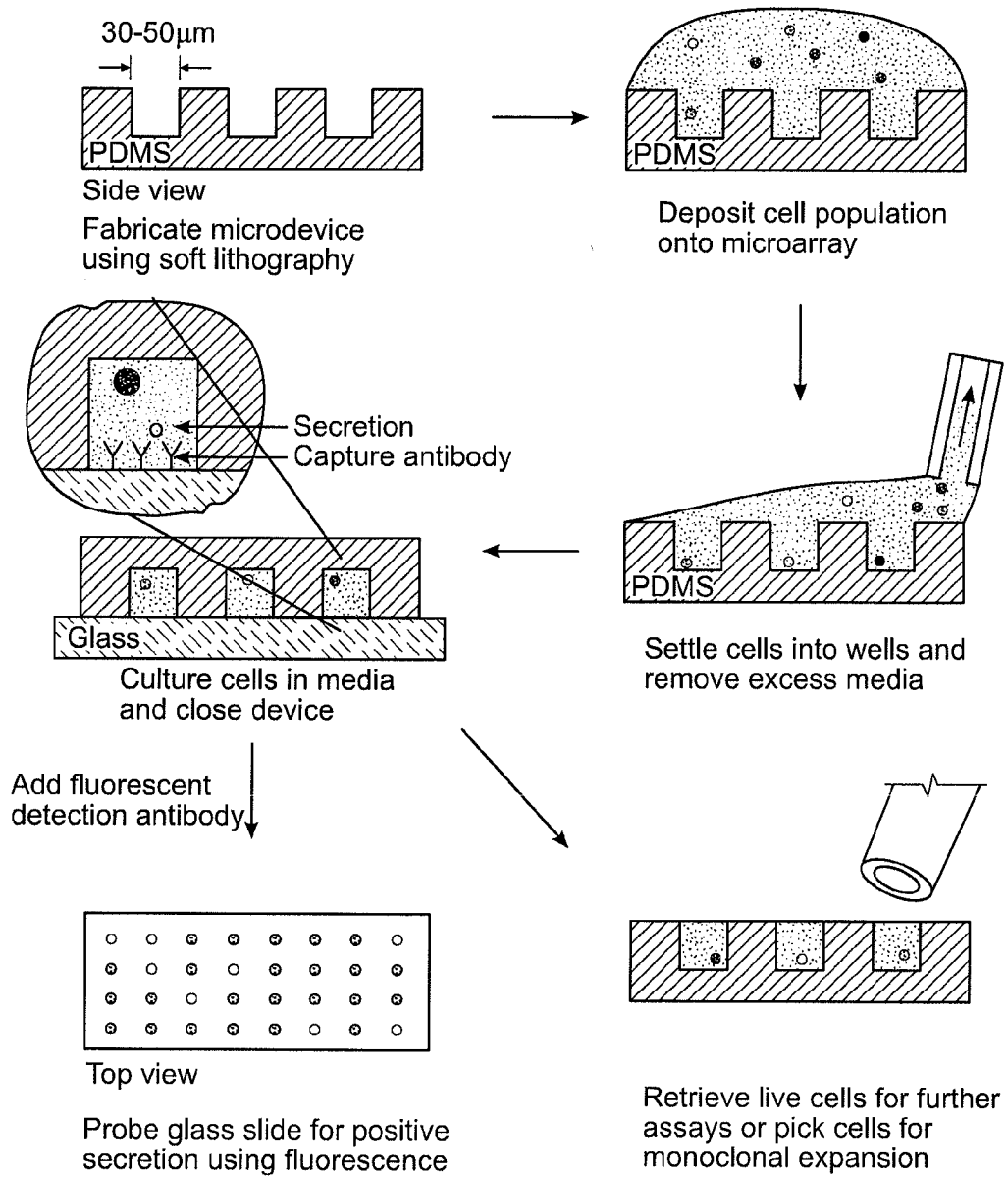
FIG. 1 is a schematic showing a microengraving technique. As shown in the drawing, cells are loaded into the microwells. The excess liquid is aspirated and the polydimethylsiloxane (PDMS) is sealed onto a glass slide functionalized with capture antibody. After incubating for 2 hours, the PDMS is removed and saved for later use. The glass slide is hybridized with detection antibody for imaging with GenePix.

The invention provides methods of detecting gene expression in single cells using subnanoliter wells. Specifically, the invention provides using an elastomeric array of subnanoliter wells to confine individual cells for massively parallel single-cell reverse transcription (RT) polymerase chain reaction (PCR) and subsequent gene-specific detection using dual-labeled gene-specific deoxyribonucleic acid (DNA) probes. The invention also provides methods to identify latent viral infection, such as cells latently infected with human immunodeficiency virus (HIV).

The relationship between expression of certain genes and the subsequent functional activities of a cell is a central question in cell biology. Traditional assays for studying genetic and proteomic responses to applied external stimuli typically require more than $10^3$ cells for each analysis (E. Engvall and P. Perlmann, 1972 J. Immunol., 109, 129-135; Chen et al., 2005 Nucleic Acids Res., 33, e179). However, the resulting average measures obscure variations that may exist among individual cells, and can lead to misinterpretations of the biology (Bengtsson et al., 2008 BMC Molecular Biology, 9, 63; D. Di Carlo and L. P. Lee, 2006 Anal. Chem., 78, 7918-7925). Analytic tools for assessing both gene expression and cellular functions, such as secretion of particular proteins, for the same individual cells would allow direct determination of the relationships between transcription and biological activities. Described herein is a one-step process for detecting the expression of specific genes in thousands of single cells in parallel, and demonstrates how this process—combined with imaging cytometry and microengraving (Ogunniyi et al., 2009 Nat. Protoc., 4, 767-782; Han et al., Lab Chip, 2010, 10, 1391-1400)—enables an integrated single-cell analysis of both the expression of a specific gene and secretion of the corresponding translated protein from each cell.

The detection of transcribed genes often uses RT PCR to convert messenger ribonucleic acid (mRNA) into many copies of complementary deoxyribonucleic acid (cDNA). This reaction amplifies many specific transcripts from single cells—usually sorted into microtiter plates by flow cytometry or micromanipulation—to recover particular genes of interest (Yamamura et al., 2005 Anal. Chem., 77, 8050-8056) or to quantify the amount of mRNA present (Warren et al., 2006 Proc. Natl. Acad. Sci. U.S.A., 103, 17807-17812). Using conventional plates is labor-intensive and costly for analyzing statistically robust numbers of single cells. As described herein, to establish a single-cell methodology for detecting latent infection, RT-PCR must be efficient in picoliter volumes. Miniaturized systems have been developed that use actuated microfluidic systems (Warren et al., 2006 Proc. Natl. Acad. Sci. U.S.A., 103, 17807-17812, micro-droplets of water-in-oil emulsions (Beer et al., 2007 Anal. Chem., 79, 8471-8475; Kiss et al., 2008 Anal. Chem., 80, 8975-8981; and Mazutis et al., 2009 Anal. Chem., 81, 4813-4821) and arrays of microwells (Leamon et al., 2003 Electrophoresis, 24, 3769-3777; Lindstrom et al., 2009 Lab Chip, 9, 3465-3471; and Nagai et al., 2001 Anal. Chem., 73, 1043-1047) to define individual PCR reactions requiring only femtoliters to nano-liters of reagents to reduce costs. On-chip RT-PCR reactions have been demonstrated for amplifying isolated mRNA (Marcus et al., 2006 Anal. Chem., 78, 3084-3089; Marcus et al., 2006 Anal. Chem., 78, 956-958) or small numbers of individual cells (Toriello et al., 2008 Proc. Natl. Acad. Sci. U.S.A., 105, 20173-20178; Kumaresan et al., 2008 Anal. Chem., 80, 3522-3529). Recently, it has been demonstrated that 72 parallel PCR reactions in 450 pL volumes on a microfluidic chip was possible (Warren et al., 2006 Proc Natl Acad Sci U.S.A., 103 (47), 17807-17812). Real time RT-PCR has also been performed in 1241 oil droplets with volume (70 pL) containing viral RNA (Beer et al., 2008 Anal Chem, 80 (6), 1854-1858). Using a modified PCR reaction, the 454 sequencing in 75 pL silicon wells has sequenced about one million transcripts on beads (Leamon et al., 2003 Electrophoresis, 24 (21), 3769-3777; Margulies et al., 2005 Nature, 437 (7057), 376-3 80). Finally, RT-PCR has been performed directly from single cells without purifying the mRNA in 20 microliter volumes (Wang, X. and Stollar, B. D. 2000 J Immunol Methods, 244 (1-2), 2 17-225). However, prior to the invention described herein, there was no technique for the one-step, high-throughput, single-cell RT-PCR in picoliter volumes in a single well.

The paucity of single-cell RT-PCR studies has been attributed to the laborious and difficult task of purifying mRNA from individual cells and subsequently synthesizing and purifying total single-cell cDNA (Liss et al., 2002 Nucleic Acids Res., 30: e89). The difficulty is due to the loss of material during the subsequent steps of cell isolation, lysis, mRNA isolation, and cDNA synthesis. Reasons for the loss include mRNA degradation due to ribonucleases (RNases) or damage, nonspecific adhesion to the reaction vessel, and reverse transcription not going to completion (Marcus et al., 2006 Anal. Chem., 78: 3084-3089). Given the relatively high concentration of deoxyribonucleases (DNases) and RNases in small reaction volumes following lysis or rupture of a cell, prior to the invention described herein, those skilled in the art would believe that DNA and RNA would be degraded by DNases and RNases, respectively. It would be expected that, even in the presence of inhibitors, undesired RNase would chew up any available RNA template before or during reverse transcription of the template into cDNA. Similarly, resident DNases would be expected to degrade any cDNA that was successfully generated via reverse transcription. Unexpectedly, as described below, the addition of the RNase inhibitor, SUPERASE IN™ RNase inhibitor, was able to successfully prevent mass degradation of the RNA template in small volumes. Surprisingly, the methods described herein utilized an elastomeric array of sub-nanoliter wells to confine single cells for successful massively parallel single cell RT-PCR and subsequent gene-specific detection using dual-labeled, gene-specific DNA probes (Holland et al., 1991 Proc. Natl. Acad. Sci. U.S.A., 88, 7276-7280). One potential explanation for the method's unexpected success is that given the high effective template concentration, the rate of DNase and RNase-driven degradation is overcome by the relatively faster rate of reverse transcription and PCR.

Unlike previous methods that utilized multi-step microfluidic devices with several reagent and reaction reservoirs to perform off-chip RT-PCR on mRNA isolated from single cells (Marcus et al., 2006 Anal. Chem., 78: 3084-3089), the methods described herein allow for RT-PCR and subsequent gene-specific detection to take place in one step on a single cell in a single well. In other words, unlike previous methods wherein cell capture, cell lysis, mRNA purification, cDNA synthesis, and cDNA purification were sequentially performed in different flow channels throughout a microfluidic devise, the methods described herein do not require multiple inputs and outputs to introduce and remove various reagents from the device. By contrast, the methods described herein enable one-step, single-cell, RT-PCR in a small volume in a single well. For example, as described herein, the reaction is performed in a volume less than 1 µL, e.g., less than 1 nL, less than 500 pL, less than 250 pL, or about 125 pL. The RT-PCR assay presented here allows for the detection of gene expression in thousands of individual cells in parallel with high sensitivity and specificity. A significant advantage of the approach is that it integrates with other processes for single-cell analysis such as microengraving and image-based cytometry. This combination provides a multivariate and direct measure of the relationships between the presence of transcribed genes and functional cellular activities for many individual cells. Another advantage of this assay system is the speed by which results are obtained (or the assay is completed). For example, results are obtained (or the assay is completed) in less than 24 hours, less than 12 hours, or less than 10 hours. For example, the results are obtained (or the assay is completed) in less than 4 hours.

The methods described herein are well-suited to evaluate simple relationships between the transcription of genes and the secretion of the translated products—useful intersection to evaluate the suitability of surrogate markers for monitoring clonal production in biomanufacturing or clinical factors in diagnostics. Other applications for this approach include the detection and functional phenotyping of cells infected with retroviruses (e.g., HIV, human T cell leukemia virus (HTLV), herpes simplex virus (HSV) 1 and 2), human endogenous retroviruses (hERV) or intracellular pathogens (e.g., *Mycobacterium tuberculosis* (tuberculosis), *Rickettsia* spp., and *Chlamydia* spp.) and the amplification of specific genes from many cells in parallel for downstream genetic analysis by sequencing.

Latent Virally Infected Cells

Despite more than twenty five years of research on the interactions between humans and the human immunodeficiency virus type 1 (HIV-1), HIV/acquired immune deficiency syndrome (AIDS) remains one of the most prevalent threats to global health. The United Nations estimates that over 33 million people are afflicted with HIV/acquired immune deficiency syndrome (AIDS), including almost 1% of the world's supposedly healthy population (ages 15-49) (UNAIDS, Executive summary: 2008 Report on the global AIDS epidemic). Current estimates suggest it will become the third leading cause of mortality worldwide over the next twenty years behind cancer and cardiovascular disease. The prevalence of persistent HIV infection is largely due to the ability of HIV to lie dormant within a cell (Han et al., 2007 Nat Rev Microbiol, 5 (2), 95-106). Highly active antiretroviral treatments (HAART) are effective at reducing HIV plasma levels below detectable levels, but upon termination of HAART, HIV RNA transcripts in the blood are measurable after 3-5 days (Han et al., 2007 Nat Rev Microbiol, 5 (2), 95-106; Chun et al., 1995 Nat Med, 1 (12), 1284-1290; Finzi et al., 1997 Science, 278 (5341), 1295-1300; Chun et al., 1997 Proc Natl Acad Sci USA, 94 (24), 13193-13197; and Wong et al., 1997 Science, 278 (5341), 1291-1295). Latently-infected cells persevere in a resting population of T cells, e.g., $CD4^+$ T cells (Chun et al., 1995 Nat Med, 1 (12), 1284-1290). Latent infections hinder the eradication of HIV, as such latent infections can persist for as long as 70 years (Finzi et al. 1999 Nat Med, 5 (5), 512-517). Identification of latent viral infection requires 1) differentiation between integrated and unintegrated viral genome in cell lysates; and 2) verification that the living cell can produce competent virus upon stimulation. While both assays can be applied to a population of cells, existing analytical methods simply are not adequate to detect latently-infected cells on a single-cell basis because each experiment precludes the performance of the other. As such, there is a pressing need for new strategies to identify latent viral infection, such as cells latently-infected with HIV.

Latently infected cells do not bud virions in a resting state, but once stimulated, these cells produce virulent virus. It is unlikely that viral proteins are produced when the virus is in its dormant state, as the small amount of HIV transcript that latently infected cells produce is premature or mislocalized (Lassen et al., 2004 J Virol, 78 (17), 9 105-9114; and Lassen et al., 2006 PLoS Pathog, 2 (7), e68). During latent infection, the HIV genome integrates into the host chromosome, as unintegrated HIV DNA is unstable and does not transcribe viable mRNA (Zhou et al., 2005 J Virol, 79 (4), 2199-2210). These characteristics render latently infected cells virtually indistinguishable from uninfected cells. Given their low frequency and their difficulty of detection, prior to the invention, it was challenging to examine latently infected cells in vitro.

Latent infections are currently identified using a population of highly purified resting T cells. These cells are often taken from patients on HAART due to the undetectable levels of HIV in their blood. During purification, flow cytometry is utilized to remove cells with markers of various stages of activation such as Cluster of Differentiation 69 (CD69), CD25, and human leukocyte antigen DR (HLA-DR). To demonstrate that latent infections exist in the population, purified cells are stimulated with phytohemagglutinin (PHA) (Hermankova et al., 2003 J Virol, 77 (13), 7383-7392), gamma-irradiated virus-free peripheral blood mononuclear cells (PBMCs) (Hermankova et al., 2003 J Virol, 77 (13), 7383-7392), or cross-linking anti-CD3 antibodies to encourage the production of new virions (Wong et al., 1997 Science, 278 (5341), 1291-1295). However, while this method is effective in HAART patients, it has failed in patients that are actively producing low levels of virus (Han et al., 2007 Nat Rev Microbiol, 5 (2), 95-106).

To verify that the population contains cells with integrated HIV genome, several assays are utilized to digest the host genomic DNA with a specific restriction enzyme. Then, the digests are diluted to allow for intramolecular ligation. In Alu PCR, one primer containing the Alu repeat element and another primer specific for HIV are used to amplify integrated DNA (Chun et al., 1997 Proc Natl Acad Sci USA, 94 (24), 13193-13197). Common integration sites are sequenced by using inverse PCR where the region flanking the HIV genome is amplified (Chun et al., 1997 Nature, 387 (6629), 183-188; Han et al., 2004 J Virol, 78 (12), 6122-6133). While these digestion assays only detect integrated HIV pro-viral DNA, they have varying efficiencies because the viral DNA integrates at different locations, rendering variable the length of the amplified sequence.

Although the presence of integrated HIV genome is necessary, it is insufficient to establish true latent infection, as not all integrated HIV genomes produce replication-competent virus after activation. Deleterious mutations during reverse transcription and integration into silenced regions of the host genome may result in the lack of competent virus production (Chun et al., 1997 Nature, 387 (6629), 183-188). The identification of latent viral infection requires 1) differentiation between integrated and unintegrated viral genome in cell lysates; and 2) verification that the living cell can produce competent virus upon stimulation. While both assays can be applied to a population of cells, existing analytical methods simply are not adequate to detect latently-infected cells on a single-cell basis because each experiment precludes the performance of the other. First, stimulated cells would produce virions that can infect and integrate into uninfected cells. Thus, it would be unclear if the integrated HIV was from previously-infected or newly-infected cells. Moreover, the process of detecting integrated HIV genome requires killing the cell, which would prevent their subsequent stimulation. Finally, latently infected cells are rare—only one cell in one million resting $CD4^+$ T cells is latently infected (Chun et al., 1997 Nature, 387 (6629), 183-188).

Recently, a method was devised that partially bypasses the conflicting assays (Monie et al., 2005 J Virol, 79 (8), 5185-5202). Resting T cells were cultured in the presence of drugs that block the reverse transcription (RT) of HIV mRNA to DNA and the integration of HIV DNA into the host genome. After stimulation, the newly produced virions that bud from latently infected cells can infect other cells, but the drugs prevent the integration of virus genome into the host. To avoid the varying transcript length of Alu PCR, HIV RNA from the media can be analyzed by RT-PCR primers specific to HIV mRNA. While this assay can detect latent infection in a population of cells, prior to the invention described herein, there was no method to detect latent infection in a single cell in a single well.

Microengraving for Single-Cell Study and its Advantages

Microengraving is a recently developed technique for rapid, high-throughput, multiplexed screening of individual cells. Preferably, the number of cells is fewer than 5 cells, e.g., fewer than 4 cells, fewer than 3 cells, fewer than 2 cells, e.g., a single cell per well. This technique has been used to screen hybridomas to produce monoclonal antibodies (Love, et al., 2006 Nat Biotechnol, 24: 703-707). It was also adapted for the multiplexed interrogation of populations of individual human peripheral blood mononuclear cells from Type 1 diabetic patients for secreted cytokines (IFN-gamma and IL-6), antigen-specific antibodies, and lineage-specific surface markers (Bradshaw, et al., 2008 Clin Immunol, 129: 10-18).

The microengraving technology is a high-throughput method that detects secreted proteins. In this technology, an array of microwells is molded into a flexible polydimethylsiloxane (PDMS) polymer stamp to isolate individual cells. For example, cells are loaded into a 1" by 3" PDMS device with 80,000 square wells, each with a 50 μm length. Alternatively, a device with 250,000 wells of 30 µm is used. By loading the PDMS device with cells and sealing the PDMS onto a glass slide, the enclosed wells are individual containers for single-cell culture (FIG. 1). To detect secreted proteins, the glass slide is functionalized with capture antibodies specific for the target protein. After 2-3 hours of incubation, the glass slide is then removed from the PDMS. Fluorescent detection antibodies are added to the glass slide while the cells in the PDMS are cultured. Positive spots are mapped back to the cell in the well, and those cells can be picked by a robot and grown into a monoclonal population. In sum, this technique adapts sandwich enzyme-linked immunosorbent assay (ELISA) to measure protein secretion at single-cell level. Besides providing the information normally given by ELISpot and FACS, this technology also has the ability to trace single cells. As described in detail below, this ability to measure cellular secretion was applied to detect the production of new virions after stimulating latent cells.

Microarrays and slabs are constructed using methods known in the art, including those described in PCT/US2006/036282 (published as WO/2007/035633) and U.S. Ser. No. 61/057,371. The contents of both of these applications are incorporated herein by reference in their entirety. As used herein, "moldable slab" refers to an apparatus which can flex, move or distort, at least in one dimension, when placed in contact with a substrate. For example, in certain configurations the moldable slab may include a material, e.g., an elastomeric material, such that as the moldable slab is placed in contact with a substrate, a substantially fluid tight seal may be formed between the moldable slab and the substrate to retard or to prevent any fluid in the moldable slab from escaping or leaking.

The microwell arrays are fabricated in polydimethylsiloxane (PDMS) using photolithography and replica molding. The depth and size of the well is preferably less than 100 µm, e.g., less than 50 µm. For example, the depth and size of the well are set to ~30 µm. O2 plasma treatment is used to both sterilize the microarray and render it hydrophilic. The plasma-treated array is immersed in phosphate buffered saline—bovine serum albumin (PBS-BSA) to preserve the hydrophilic character for subsequent use. The methods, apparatus and kits described herein may use a moldable array of microwells or chambers (e.g., less than 100 microns in diameter, or 25-100 microns in diameter) to retain one or a few cells in each microwell. The array is placed in physical contact with a substrate in such a manner that the microwells become closed containers or a test apparatus. Incubation of this system allows the cells to produce products, such as antibodies, cytokines, viruses and other secreted or released products, that are then immobilized on the substrate in the regions contacted by the microwells. In this manner, a microarray of the cellular products from each microwell is produced. After incubation of the system for a suitable time, e.g., 1, 5, 30, 40, or 50 minutes to a few hours (1, 3, 6, 12, e.g., 24 hours or less), the microwell array is removed from the substrate, and the immobilized cellular products on the substrate, the microarray or microengraving, may be screened with a known species to determine whether or not the immobilized cellular product(s) associate with the known species.

The soft lithographic technique uses a dense array of microwells (0.1-1 nL each) containing individual cells to print a corresponding array of the molecules secreted by each cell. For example, as described herein, the microwells contain a volume less than 1 µL, e.g., less than 1 nL or less than 500 pL. For example, the reaction is performed in a volume of between about 10 pL and 1,000 pL; between about 50 pL and 500 pL; or between about 100 pL and 200 pL, e.g., about 125 pL. Alternatively, the reaction is performed in a volume of between about 1 pL and 500 pL; between about 10 pL and 100 pL; between about 15 pL and 50 pL; between about 20 pL and 40 pL; between about 25 pL and 30 pL, e.g, about 27 pL.

The cells remain in culture in a microwell after the engraving, and the microarrays are interrogated in a manner similar to commercial microarrays of proteins or antibodies—for example, by use of fluorescently labeled reagents and laser-based fluorescence scanners. This method, therefore, enables rapid identification of those cells that exhibit desired properties, such as secretion of an antigen-specific antibody, and their subsequent recovery from individual wells for clonal expansion. The moldable slab is fabricated by soft lithography and replica molding and is of a biocompatible material, which is not toxic and gas permeable. The moldable slab or the substrate or both comprises one or more materials selected from the group consisting of glass, plastic, silicon, polystyrene, polycarbonate, poly(dimethylsiloxane), nitrocellulose, poly(vinylidene fluoride), and a metal. The metal is one or more of gold, palladium, platinum, silver, steel or alloys or mixtures thereof. In some embodiments, the substrate is a glass slide, a plastic slide or a bead, and the moldable slabs contain a microwell array. The moldable slab compresses against the substrate to form a tight, but reversible seal with the substrate. The microwell array comprises a block of wells where a well has a diameter of about 30 µm and a depth of about 30 µm and the wells are separated by about 30 µm, or a well has a diameter of about 50 µm and a depth of about 50 µm and the wells are separated by about 50 µm, or a well has a diameter of about 100 µm and a depth of about 100 µm and the wells are separated by about 100 µm. The wells are sized to retain about 1 nanoliter or less of fluid. Illustrative methods for producing moldable slabs are described in more detail in U.S. Pat. No. 6,180,239 and U.S. Pat. No. 6,776,094, the entire disclosure of each of which is hereby incorporated herein by reference in its entirety.

The exact number of the wells or chambers in the moldable slab may vary. In some examples, the moldable slab includes a single large microwell where a single species may be screened. For example, a moldable slab includes a single type of cell, catalyst or other selected species to be screened. In configurations where the moldable slab is configured as an array, the number of individual microwells may vary from about 1, 4, 8, 24, 48, 96, 384, 1024, 2048, 5096 or more or any value in between these illustrative values.

An engraving plate includes a plurality of wells, each of the wells is less than 100 micrometers in diameter and comprises a single cell. Preferably, the number of cells is fewer than 5 cells, e.g., fewer than 4 cells, fewer than 3 cells, fewer than 2 cells, e.g., a single cell per well. The engraving plate is a gas-permeable conformable composition. The plate has an elastic modulus (Young's Modulus) in the range of 200-2000 Kilopascal (kPa). The composition of the plate is preferably poly(dimethylsiloxane). The wells of the plate contain at least one cell. That cell is an immune cell, an antibody-producing cell, a hybridoma cell, a T cell, or other cell from the blood or a tissue. The function or secretory profile of the cell or cells is unknown.

Identification of positive associations is performed using numerous suitable techniques including, for example, fluorescence, mass spectrometry (e.g., massARRAY from Sequenom®), surface plasmon resonance, gene arrays (e.g., BeadArray from Illumina®), DNA or RNA sequencers (e.g., nanoString sequencers) or other analytical methods used in traditional immunoassays (e.g., colorimetric methods). For example, the species added to the substrate may include a fluorescent label such that if the labeled species added to the substrate associates with the material disposed on the substrate, fluorescence emission may occur. Illustrative fluorescent labels include, for example, fluorescein isothiocyanate, didansyl chloride, lanthanides and lanthanide chelates, Alexafluor® dyes, inorganic semiconductor nanocrystals (e.g., quantum dots composed of II/VI or III/V semiconductors), and similar labels. Any fluorescence emissions may be detected visually or may be detected using suitable instruments, such as fluorescence microscopes, fluorimeters, cameras, or instruments that include a charge coupled device, a photomultiplier tube, a diode array and the like. Other labels that emit light, e.g., phosphorescent labels, chemiluminescent labels, etc., may also be used and detected using similar techniques as those used in connection with fluorescence detection.

The detectable moiety added to the substrate may include a colorimetric label such that if the labeled species added to the substrate associates with the material disposed on the substrate, and after addition of a suitable enzyme substrate, a color may result. For example, a colorimetric label is an enzyme, such as horseradish peroxidase. After an enzyme substrate, such as, for example, o-phenylenediamine dihydrochloride, is added to the enzyme a colored product is produced if the colorimetric label is present. The colored product may be detected visually or may be detected using suitable instruments such as, for example, UV/Visible instruments, plate readers, etc. In some examples, the colorimetric label may be a dye, e.g., an organic or an inorganic dye, such that if association occurs, the well or chamber remains colored, whereas if no association occurs, the well or chamber is clear and colorless. For example, if no association occurs the well appears clear or nearly colorless after unassociated labeled species are removed by washing.

Other detectable markers include a radiolabel. The radiolabel may be integrated into the species or may be added as a tag to the species. When a radiolabel is used, it may be desirable to construct the substrate with an absorbing material between array members to prevent or reduce crosstalk between the various members disposed on the substrate. Illustrative radiolabels include, but are not limited to, $^3$H, $^{14}$C, $^{32}$P, $^{33}$P, $^{35}$S and $^{125}$I. The species disposed on the substrate may be radiolabeled, and upon association, any radioactive emission from the species may be quenched by a molecule or group which associates with the species disposed on the substrate. Suitable radiolabels for use in the methods, apparatus and kits disclosed herein will be readily selected by the person of ordinary skill in the art, given the benefit of this disclosure.

The relationship between the expression of particular genes in cells and their impact on phenotypic characteristics is important for understanding how cells regulate responses to their environment. Described herein is a microwell-based method to detect copies of mRNA transcripts directly from individual cells by one-step, single-cell, reverse transcription polymerase chain reaction (RT-PCR). This approach permits the detection of mRNA transcripts of interest for more than 6,000 single cells in parallel per assay with high sensitivity and specificity for constitutively active genes. This method was combined with microengraving and image-based cytometry to examine the relationships between gene expression and cellular secretion of antibodies in a clonal population. As described in detail below, most individual human B cell hybridomas transcribed a requisite gene for their antibodies, but only a subset of those cells secreted the antibody. The technique described herein allows for the detection of replicating intracellular pathogens such as retroviruses.

EXAMPLE 1

Figure 2A:
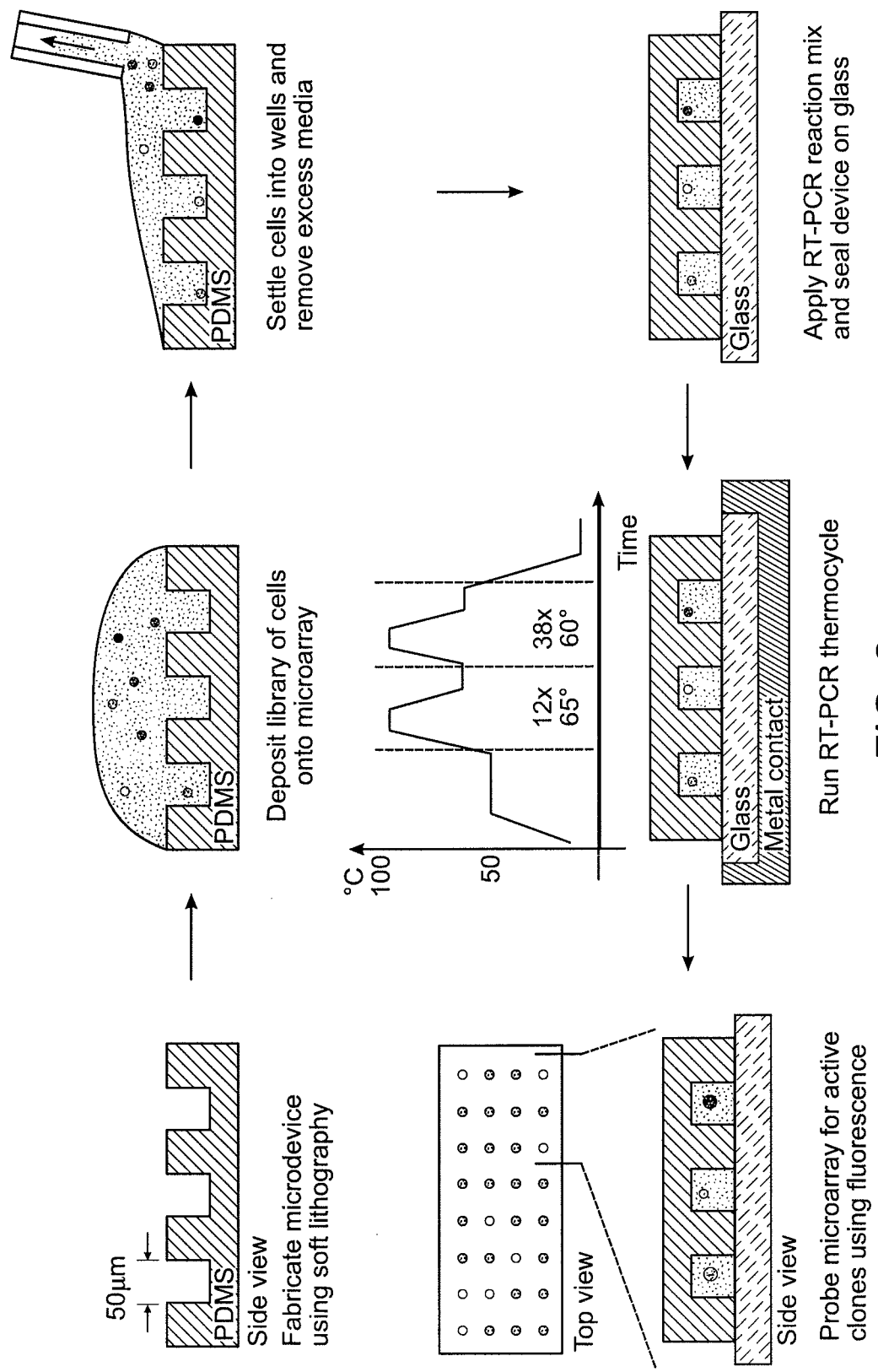
FIG. 2a is a schematic illustrating a method for parallel single-cell reverse transcription (RT) polymerase chain reaction (PCR) RT-PCR reactions in subnanoliter volumes. As shown in the drawing, cells are deposited in microwells, filled with a solution of components for RT-PCR, and then sealed to a glass slide. The thermal lysis, first strand synthesis, and amplification of complementary deoxyribonucleic acid (cDNA) are conducted on a thermocycler. The fluorescence intensity of cleaved probes is detected by epifluorescent microscopy.

Development of Multiplexed RT-PCR in Microwells for High-Throughput Screening of Active Transcripts Detecting latently infected cells requires the demonstration that the cells do not initially produce virus. Also, in studying single cell expressions, a method to physically isolate each cell is required. To this end, microwells serve as containers for each cell so that single cells are analyzed independently of their neighbors (FIG. 2a).

Fabrication and Design of Elastomeric Arrays of Microwells

Silicon masters for 50 µm wells were produced by photolithography (Stanford Microfluidics Foundry, Palo Alto, Calif.). Each chip fits on a standard glass slide (75×25 mm2, Corning, Lowell, Mass.) and has an array of 72×24 blocks of wells. Each block of wells contains a 7×7 grid of 50×50×50 µm3 microwells. For every four blocks, a channel was included to facilitate liquid removal by aspiration from the device. Approximately 5 nL of polydimethylsiloxane (PDMS; Sylgard 184 Silicone Elastomer Kit, Dow Corning, Midland, Mich.) was injected into a mold so that the final device has a thickness of 1 mm and is attached to a standard glass slide. PDMS was mixed at a mass ratio of 10:1 elastomer base to curing agent, deaerated for 20 min under vacuum, and cured for 2 hr at 80° C.

Cell Culture

Epstein-Barr virus transformed human hybridoma 4D20 cells were cultured in RPMI 1640 (Mediatech, Manassas, Va.) supplemented with 20% fetal bovine serum (FBS; PAA Laboratories, New Bedford, Mass.), 2 mM L-glutamine (Mediatech), and 1× Penicillin-Streptomycin (Mediatech). The cell lines were maintained in 25 mm2 canted-neck flasks (BD Falcon, BD Biosciences, San Diego, Calif.) in 5% CO2 at 37° C. and were split every three days to $2.5 \times 10^5$ cells/mL.

Cell Preparation and Loading

Cells were split the day before their use in experiments. For cell labeling, the cells were first washed once with phosphate buffered saline (PBS; Mediatech), then resuspended in 1 nL PBS with 1 µL of the labeling dye (CellTracker Violet BMQC, Life Technologies, Carlsbad, Calif.) according to the manufacturer's recommended concentration. Labeling was carried out at 37° C. for 30 min. Cells with high-viability were isolated with Ficoll-Paque Plus (GE Healthcare Biosciences, Pittsburgh, Pa.) and then treated with 30 µg/mL bovine pancreatic RNase A (Sigma-Aldrich, St. Louis, Mo.) at 37° C. for 30 min. The cells were then washed three times with 10% FBS in RPMI and once with PBS before they were resuspended in 5 nL PBS. After these steps, more than 98% of the cells remained viable as determined by the cellular exclusion of trypan blue (Life Technologies). Each array of microwells was cleaned by a 30 s plasma treatment (Plasma Cleaner PDC-32G, Harrick Plasma, Ithaca, N.Y.) and blocked in 0.5% BSA in PBS for 30 min at room temperature before loaded with cells by gravity such that about 50% of the wells had cells in them.

RT-PCR Amplification from Single Cells

Primers and dual-labeled TAQMAN® probes for housekeeping genes were designed using the online software RealTimeDesign (Biosearch Technologies, Novato, Calif.). The primer and probe sequences (Biosearch Technologies) were as follows, from 5' to 3':

TCCAGCGTACTCCAAAGATTCAG, (B2M forward; SEQ ID NO: 2)

GAAACCCAGACACATAGCAATTCAG, (B2M reverse; SEQ ID NO: 1)

FAM-CTCACGTCATCCAGCAGAGAATGGA-BHQ1, (B2M probe; SEQ ID NO: 7)

TTGCCCTCAACGACCACTTTG, (GAPDH forward; SEQ ID NO: 8)

GAGGTCCACCACCCTGTT, (GAPDH reverse; SEQ ID NO: 9)

FAM-TCCTGGTATGACAACGAATTTGGCTACA-BHQ1, (GAPDH probe; SEQ ID NO: 10)

GATGCAGAAGGAGATCACTGC, (ACTB forward; SEQ ID NO: 11)

GCCGATCCACACGGAGTA, (ACTB reverse; SEQ ID NO: 12)

FAM-CAAGATCATTGCTCCTCCTGAGCGC-BHQ1, (ACTB probe; SEQ ID NO: 13)

GGTCCTGTGCTGGTGAAAC, (4D20 Heavy Chain forward; SEQ ID NO: 14)

GCTCACACCCATTCTATCATTG, (4D20 Heavy Chain reverse; SEQ ID NO: 15)

Quasar670-CACAGAGACCCTCACGGTGACCT-BHQ2. (4D20 Heavy Chain probe; SEQ ID NO: 16)

The reaction mix used the qScript One-Step Fast qRT-PCR kit with ROX (Quanta Biosciences, Gaithersburg, Md.). It contained 1× One-Step Fast Master Mix with ROX, 1 μM of each primer, 200 nM of probe, 1x qScript One-Step Fast RT, 80 U of SUPERASE IN™ RNase Inhibitor (Life Technologies), and 0.05% NP40 (Sigma) in a total volume of 40 μL per array. The reaction mix was applied to the microwells and spread using a pipet tip before the device was sealed onto another glass slide. Excess reaction mixture was removed along the sides and the entire device was placed on an Eppendorf Mastercycler Gradient (Eppendorf, Hamburg, Germany) with a glass slide adaptor (in situ Adapter, Eppendorf). Mineral oil (Sigma) was added to improve the heat conductivity between the adaptor and the device. The thermocycling profile was 40 min at 50° C., 2 min at 95° C., 12 cycles of 40 s at 95° C. and 1 min at 65° C., and 38 cycles of 40 s at 95° C. and 1 min at 60° C., with the lid maintained at 50° C. It was common to observe dried wells around the perimeter of the array.

Microscopy

After the thermocycle, the array of microwells was imaged on an automated epifluorescent microscope (Observer.Z1; Carl Zeiss GmbH, Jena, Germany) at 10× magnification (Objective EC "Plan-Neofluar" 10×/0.3, Carl Zeiss GmbH). A broad spectrum light source was produced by a xenon lamp in a Lambda DG-4 (Sutter Instrument, Novato, Calif.) and passed through a "Pinkel" quad-band filter set (Semrock, Rochester, N.Y.) for specific excitation bandwidths. Images were captured using an EM-CCD digital camera (C9100-13, Hamamatsu Photonics, Hamamatsu, Japan). The entire system was controlled using the software AxioVision version 4.7 (Carl Zeiss GmbH).

Data Analysis

Images generated by automated microscopy were analyzed using custom software. The location, the number of cells, and the fluorescence intensity of each channel were tabulated in a text file. These information were filtered and plotted using MATLAB (MathWorks, Natick, Mass.). The data were filtered to remove wells with more than four cells (inaccurate measures of the well intensity). Wells with large variation in the reference channel (greater than two standard deviations from the mean reference signal) were also removed to eliminate wells with no liquid and wells with a high degree of covariance in fluorescence. For each block of wells, the mean gene-specific fluorescence intensity of empty wells ($I_{empty}$) was calculated and used to determine the relative fluorescence of every well ($I_{well}/I_{empty}$). A histogram was plotted to bin the relative fluorescence intensities. The histogram peak for $I_{well}/I_{empty}$ of empty wells was fit to a Gaussian curve to compute estimated values for the mean and standard deviation of negative reactions. The threshold value on the relative fluorescence for positive reactions was set to be three standard deviations above the mean. From this value (e.g., $I_{well}/I_{empty}=1.4$), the sensitivity, specificity, and positive predictive value were determined for each gene.

Combination of Microengraving and RT-PCR

Detailed procedures for microengraving can be found in Ogunniyi et al. Nature Protocols (2009) vol. 4 (5) pp. 767-82. Briefly, cells were labeled with CellTracker Violet, loaded into the microwells, and imaged. The microwells were then sealed with a glass slide that was functionalized with anti-IgG1 antibodies at 37° C. After 2 hr, the glass slide was separated from the microwells and captured IgG1 was detected following the application of a secondary antibody (goat-anti-human-IgG1) conjugated with Alexa Fluor 647 (Life Technologies). RT-PCR was then performed on the cells in the microwells. Data from the microscopy, microengraving, and RT-PCR were collected and filtered. Only wells that contained a single live cell initially, and had a single cell after RT-PCR (detected by non-specific staining with the reference dye, ROX) were tabulated. Spots on the microarray generated by microengraving that had a signal-to-noise ratio greater than 2 for more than 55% of its pixels and a coefficient of variation less than 80 were considered positive for IgG1 secretion.

Studies have previously described a high-throughput assay to functionally characterize large numbers of primary cells by loading single cells in picoliter microwells (~2×10$^5$ per microarray, each well ~30 μm diameter) (Bradshaw et al., 2008 Clin. Immunol., 129(1), 10; Love et al., 2006 Nat. Biotech., 24(6), 703). Not only are microwells used as containers for the RT-PCR reactions, but they are also be used to separate a population of cells into single cell entities. Using a larger array or multiple slides allows for the separation and identification of rare cells in a population of millions of cells. After loading, excess cells are aspirated and RT-PCR reaction mix is added. During the thermocycle, cells are lysed for efficient reaction to occur. As described below, HIV production is analyzed by microengraving before RT-PCR and genetic mutations that cause drug-resistance are sequenced after RT-PCR. All images are analyzed by CellProfiler (Carpenter et al., 2006 Genome Biol, 7 (10), R100) and Matlab. Reagents for RT-PCR reactions that integrate the lysis of mammalian cells, reverse transcription, and the amplification of the cDNA into a single operation are widely available commercially. Described below is a method using an elastomeric array of subnanoliter wells to confine individual cells for massively parallel single-cell RT-PCR and subsequent gene-specific detection using dual-labeled, gene-specific DNA probes (Holland et al., 1991 Proc. Natl. Acad. Sci. U.S.A., 88, 7276-7280) (TAQMAN® probes) (FIG. 2a).

Because beta-2-microglobulin (B2M) is constitutively expressed in cells, it served as an ideal transcript for initial detection. B2M primers and TAQMAN® probes were designed to reverse transcribe bases 122 to 211 from the mature mRNA (GENBANK NM 004048 (GI:37704380); incorporated herein by reference). The reverse primer 5'-GAAACCCAGACACATAGCAATTCAG-3' (SEQ ID NO: 1) was also created for the complementary DNA (cDNA) in the reverse transcription step. The forward primer 5'-TCCAGCGTACTCCAAAGATTCAG-3' (SEQ ID NO: 2) was designed to be intron-spanning to reduce the amplification of genomic DNA. The TAQMAN® detection probe 5'-CTCACGTCATCCAGCAGAGAATGGA-3' (SEQ ID NO: 3) has 5-carboxyfluorescein (FAM; Absorbance: 495 nm, Emission: 520 nm) at the 5' end and Black Hole Quencher-1 (BHQ) at the 3' end, so that intact probes do not fluoresce. As the PCR reaction progresses, fluorescence is detected because the exonuclease property of Taq polymerase digests the probe and FAM is no longer at the appropriate distance from the quencher.

Several design considerations were addressed before translating the RT-PCR reaction from a typical 20 µl tube to an array of 125 pL reactors. First, the PDMS and the glass slide were blocked with bovine serum albumin (BSA) to reduce the non-specific adhesion to the well walls. BSA was also added to the reaction mixture for further reduction of non-specific binding. Given the relatively high concentration of deoxyribonucleases (DNases) and ribonucleases (RNases) in small reaction volumes, prior to the invention described herein, those skilled in the art would believe that DNA and RNA would be degraded by DNases and RNases, respectively. It would be expected that, even in the presence of inhibitors, undesired RNase would chew up any available RNA template before or during reverse transcription into cDNA. Similarly, resident DNases would be expected to degrade any complementary DNA that is successfully generated via reverse transcription. Unexpectedly, the addition of the RNase inhibitor, SUPERASE IN™ RNase inhibitor, was able to successfully prevent mass degradation of the RNA template. Finally, to ensure good heat conduction, mineral oil was added between the glass and the metal contact adapted for glass slides on the thermocycler. A COMSOL Multiphysics model for heat conduction through the glass slide demonstrated that an additional 10 seconds was needed for the wells to reach the desired temperatures at the beginning of any step.

Cells were deposited from a suspension onto the array and allowed to settle by gravity to a density of ~1 cell per well (Han et al., 2010 Lab Chip, 10, 1391-1400). After aspirating the excess liquid from the surface of the array, a 40 µL solution containing reverse transcriptase, Taq polymerase, detergent (NP-40), RNase inhibitor, gene-specific sets of TAQMAN® probe and primers, and a reference dye (5-carboxy-X-rhodamine, ROX) was dispersed over the array of wells. The wells were then sealed by placing a glass slide on top of the wells to constrain the cells in individual volumes of 125 pL for lysis and RT-PCR.

Figure 2B:
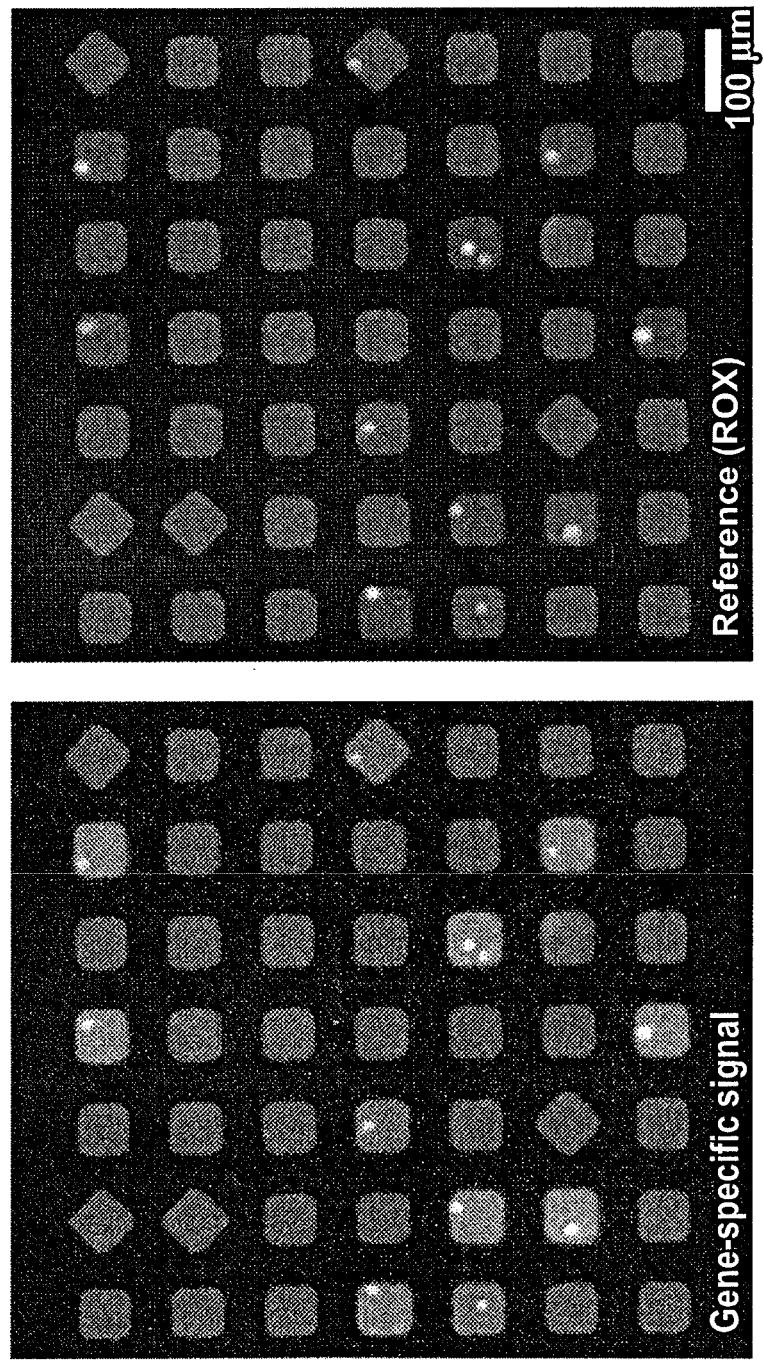
FIG. 2b is a series of fluorescent micrographs of gene-specific β-2-microglobulin (B2M) and a reference signal 5-carboxy-X-rhodamine (ROX) confined in individual, sealed microwells.
Figure 2C:
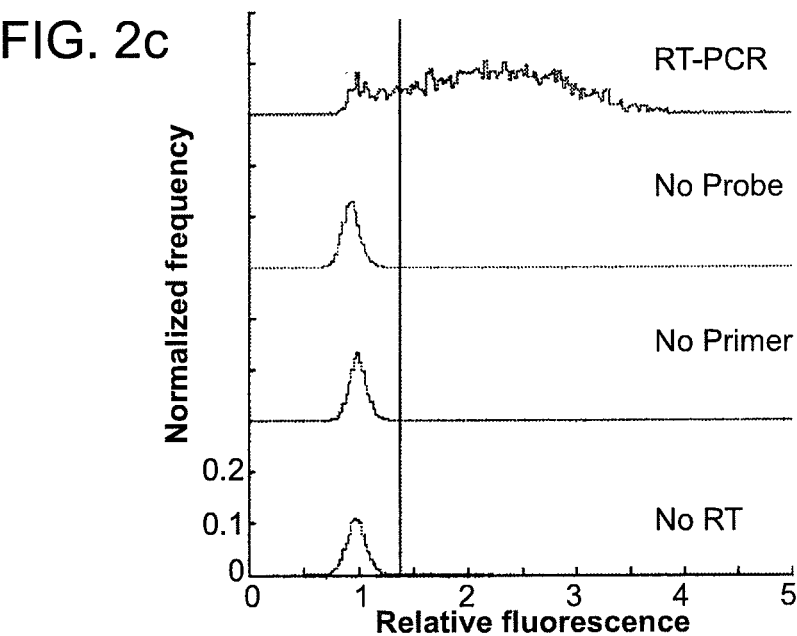
FIG. 2c is a histogram showing the relative fluorescence of wells that contain cells. Positive reactions have a relative fluorescence greater than 1.4.

To establish the feasibility for in situ lysis and detection of an expressed gene of interest in wells containing cells, a human B cell hybridoma (4D20) that produces an antibody (IgG1) against the 1918 H1N1 influenza A virus was used (Yu et al., 2008 Nature, 455, 532-536). Lysis of the cells and subsequent reverse transcription of a constitutively expressed gene B2M was achieved in the closed reactors at 50° C. for 40 min. Then, the array was subjected to 50 rounds of thermocycling to amplify the transcribed cDNA and hydrolyze the quenched fluorophore from the labeled probes. The array was imaged to detect the fluorescent signals evolved from the digested probes (FIG. 2b). The images were analyzed using a custom program to determine the location of each well, the number of cells per well, and the fluorescence intensities of both the released probe and reference dye. These data were then filtered to discard wells with no liquid after thermocycling, wells with more than four cells, and wells with a large coefficient of variation in the soluble reference signal (ROX). To normalize for regional variations of the measured intensities, the relative fluorescence was calculated as the ratio of the gene-specific signal ($I_{well}$) to the mean of the gene-specific signal of nearby empty wells ($I_{empty}$) (FIG. 2c, top).

To determine the threshold value for a positive RT-PCR reaction, the relative fluorescence of the wells containing no cells was fit to a single Gaussian distribution to obtain estimates for the mean and standard deviation of the peak representing negative reactions (0.96±0.12). Positive reactions were defined as those wells containing cells with a ratio greater than three standard deviations above the mean ratio determined for empty wells. The percentage of positive events scored in control experiments in which either the primers, probe, or reverse transcriptase were excluded was less than 0.01% (FIG. 2c). The lack of positive events scored upon omission of reverse transcriptase from the reaction indicates that the genomic DNA was not amplified, and implies that it is not necessary to remove residual genomic DNA from the reaction when using intron-spanning primers. Digestion of the gene-specific probe with DNase I in the reaction mixture prior to application to an array without cells yielded a measured ratio of probe specific fluorescence to that for the reference dye (ROX) of $I_{well}/I_{ROX}$=2.65±0.08 (data not shown). Small variations in volumes due to evaporation during the thermocycle of cell-based experiments could increase the concentration of the dye in the microwells, and thus account for the increased ratios observed, relative to the values determined by cell-free digestion of the probe. This experiment, in combination with the cell-based experiments, suggested that the maximum relative fluorescence for a positive reaction can reach an endpoint significantly greater than the ratio measured in unamplified wells (~1) within 50 rounds of thermocycling.

Figure 3:
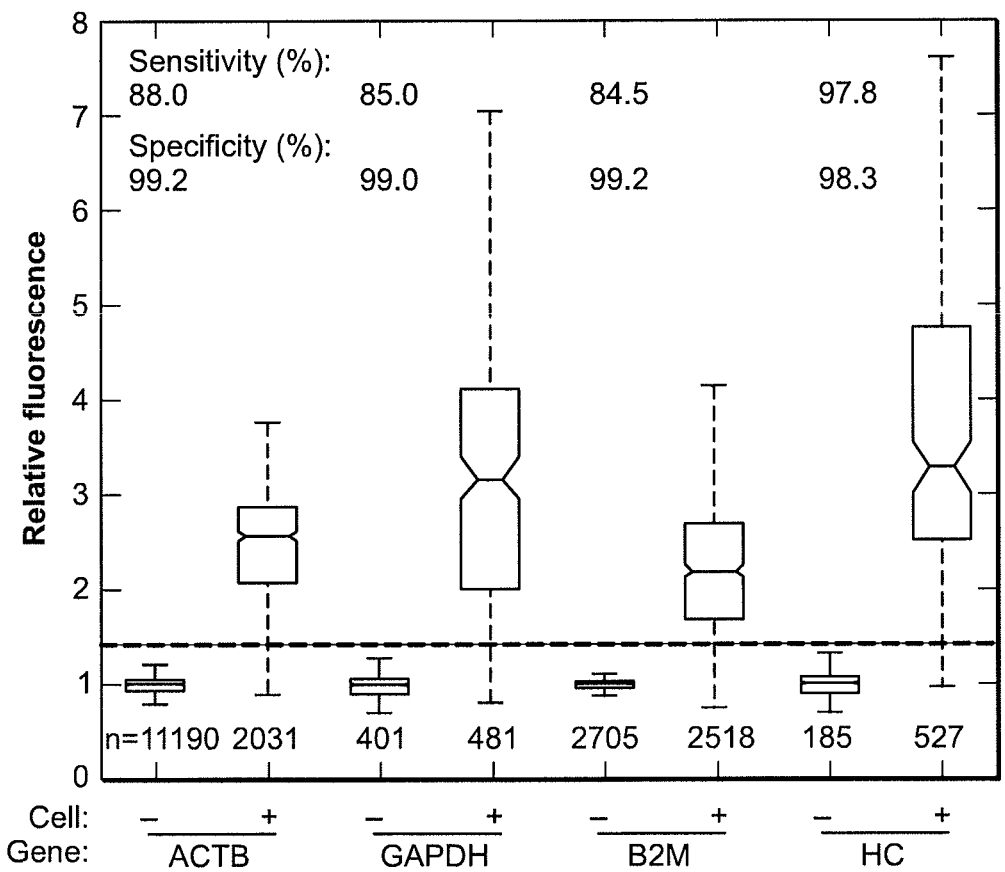
FIG. 3 is a box plot showing the detection of mRNA transcripts of constitutively expressed genes in a human B cell hybridoma (4D20 cells). The boxplots are representative of Iwell/Iempty for four genes (beta-actin (ACTB), glyceraldehyde 3-phosphate dehydrogenase (GAPDH), B2M, and 4D20 hybridomas (HC)). The boxplot follows Tukey's convention. The median is marked with a red line, and the upper and lower edges of the box indicate the values of the upper and lower quartiles. Notches on the box adjacent to the median value represent its 5% significance level. Whiskers extending from each end of the box represent extreme values within 1.5 times the interquartile range. The numbers of wells included in each box are indicated below each one. The red dashed line indicates the minimum value for positive reactions used for all four genes.

Next, the sensitivity and specificity of the method was determined using three genes that are commonly employed as standards for RT-qPCR (B2M, glyceraldehyde 3-phosphate dehydrogenase (GAPDH), beta-actin (ACTB)), as well as the heavy chain of the antibody produced by the 4D20 hybridomas (HC) (FIG. 3). The threshold values for positive reactions were determined for all four genes, and the sensitivity and specificity were calculated based on the assumption that each cell should express each gene constitutively. Using the maximum threshold of 1.4, the sensitivity and specificity of the assay were greater than 84% and 98%, respectively. These values were consistent across independent experiments. For example, the sensitivity and specificity calculated for the 4D20 HC ranged from 93.7% to 98.0%, and from 98.1% to 99.7%, respectively. The actual sensitivity could be higher than determined, as it is possible that a small fraction of the cells were not expressing the target gene at the time of the assay. The positive predictive value, which indicates the confidence in the assignments, was greater than 95% for all genes.

Figure 4:
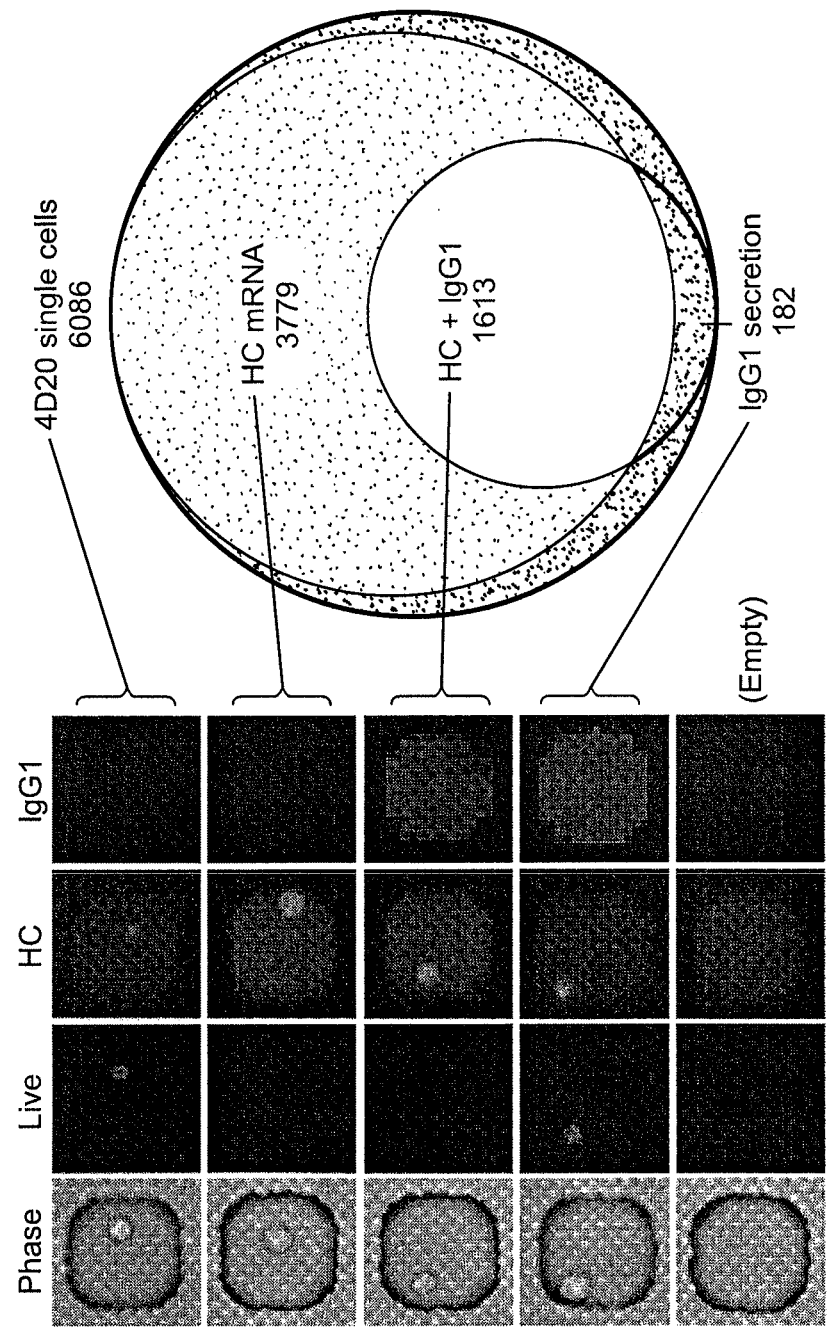
FIG. 4 is a graphic profile and schematic depicting integrated single-cell analysis of gene expression and secreted antibodies from human B cell hybridomas. 4D20 cells were labeled with a live cell stain (Celltracker Violet) and interrogated for IgG1 secretion and heavy chain mRNA. Sample images of correlated data for representative phenotypes are shown (left). The relative fluorescence of the RT-PCR is false colored from red-orange (no reaction) to green (positive reaction). Positive IgG1 secretion is false colored red. The graphic profile (right) shows the distribution of phenotypes measured. The area of each circle is proportional to the number of each phenotype enumerated.

For integrated single-cell analysis of both gene expression and secretory phenotypes, the method described here can be combined with other microwell-based techniques such as imaging cytometry and microengraving—a technique for quantifying the frequencies and rates of secretion of proteins for populations of single cells (Han et al., 2010 Lab Chip, 10, 1391-1400). It was determined if the detection of transcripts for HC in the hybridomas correlated with antibody secretion in the period of time immediately beforehand. To examine this relationship between transcribed genes and secreted proteins, 4D20 cells were labeled with a live cell marker, loaded into microwells, and imaged to quantify the number of cells in each well. The array containing cells was then sealed with a functionalized glass slide to capture secreted antibodies by microengraving (Ogunniyi et al., 2009 Nat. Protoc., 4, 767-782). After two hours, the glass slide was removed and probed for captured antibodies, while the cells in the microwells were then subjected to on-chip RT-PCR to detect HC mRNA (FIG. 4). Out of 6,086 wells with single cells, 5,392 cells (88.6%) expressed the heavy chain mRNA, but only 1,795 cells (29.5%) secreted IgG1 during the preceding period of time. Most of the cells secreting IgG1 also had detectable transcripts (89.9%). Although the analysis included only live cells at the beginning of the assay, the additional interrogation for secreted antibodies may have decreased the number of viable cells available after microengraving, and could account for the small reduction in sensitivity observed in this integrated assay relative to that seen with freshly deposited cells. Nonetheless, these data provide direct evidence that analyzing transcribed genes alone does not necessarily provide a suitable surrogate for complex functional activities such as secretion.

The above-mentioned measures of gene expression were not quantitative; however, the number of fluorescent labels that can be distinguished distinctly (~4-6 for most fluorescent microscopes) would quantify the number of transcripts detected per cell. Real-time imaging and advanced imaging methods would also quantify gene expression.

EXAMPLE 2

Multiplexed RT-PCR to Determine the Frequency and Identify of HIV Reservoirs

Multiplexed RT-PCR is developed to determine the identity and frequency of HIV reservoirs. The primers and TAQMAN® probe are designed to detect gag transcripts, which makes several mature peptides including p24, the core HIV capsid protein. Drawing from previous studies, one set of possible primers and probes are 5'-GCCCCTAG-GAAAAAGGGCTGTTGG-3' (SEQ ID NO: 4) and 5'-TACTGACGCTCTCGCACC-3' (SEQ ID NO: 5) for the forward and reverse primers, respectively, and 5'-TGAAA-GATTGTACTGAGAGACAGG-3' (SEQ ID NO:6) for the probe (Monie et al., 2005 J Virol, 79 (8), 5185-5202; Malnati et al., 2008 Nat Protoc, 3(7), 1240-1248). These sequences have been shown to bind to highly conserved regions of the gag gene. The probe has 5' Quasar 670 (Absorbance: 647 nm, Emission: 670 nm), which is quenched by 3' Black Hole Quencher-2. The fluorescent spectrum of Quasar 670 does not overlap with that of FAM, the fluorescent reporter used for the B2M probe. Therefore, fluorescent leakage between the two channels is not a problem. Significant amplification bias can favor the amplification of one transcript over another and give unrepresentative levels of the transcript, thereby leading to false negatives. Differences in amplification levels are detected by testing each primer set individually before combining them in a multiplexed reaction.

Figure 6:
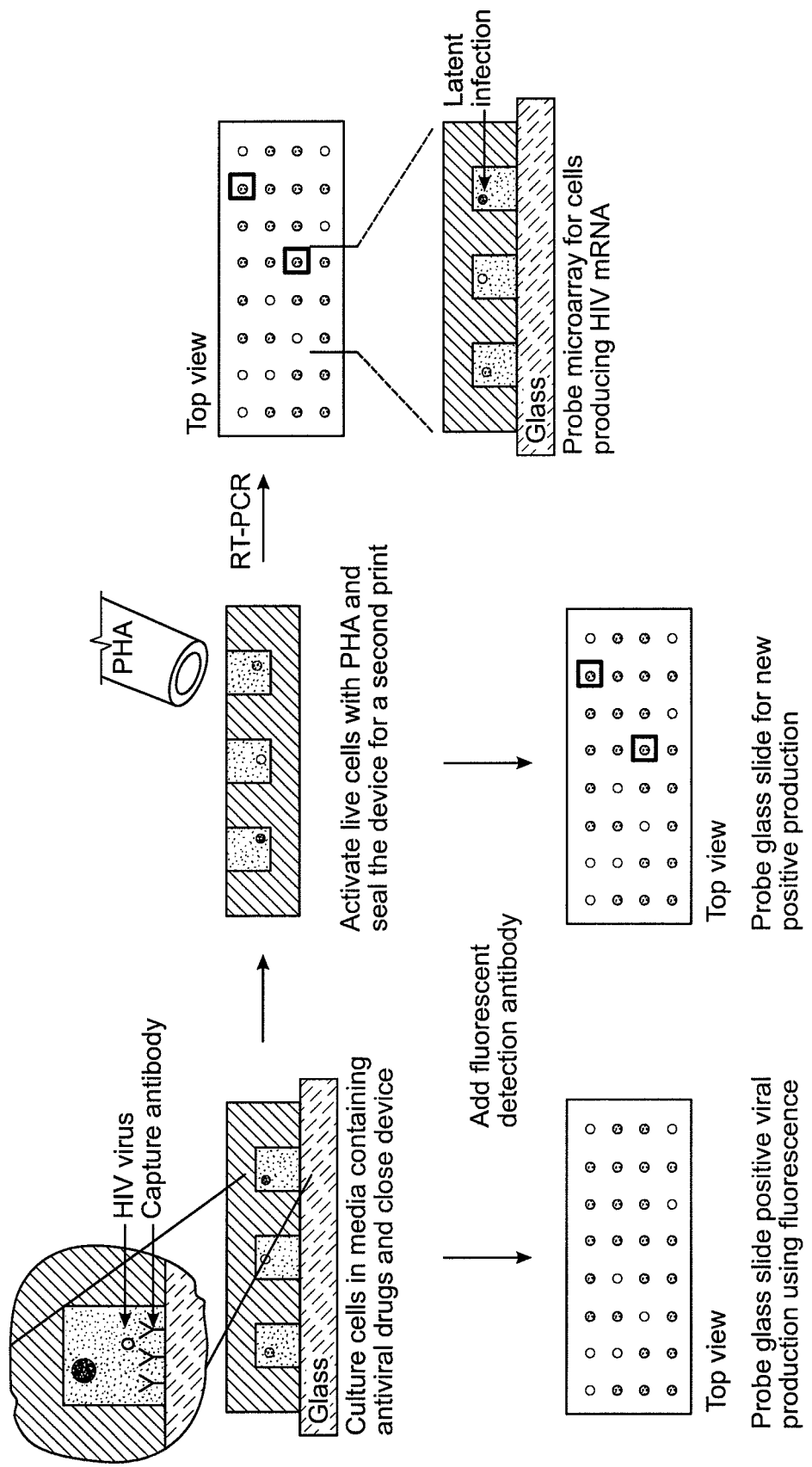
FIG. 6 is a schematic illustrating a single-cell assay for the identification of latently infected cells with RT-PCR and microengraving.

Microengraving is used to assess the frequency of HIV production in cell populations by detecting p24. Alternatively, if the cells do not produce enough virus particles for detection within that time period, multiplexed RT-PCR as previously described is performed.
Determination of Actively Producing HIV Cell Frequency In late-stage HIV infection when the CD4$^+$ population has been depleted, the cell type that is producing virus is unclear. Previous studies have shown that follicular dendritic cells in lymphoid tissue and progenitor cells of monocyte-macrophage lineage are some of the key producers (Schacker et al., 2000 J Infect Dis, 181 (1), 354-357; Zhu et al., 2002 J Virol, 76 (2), 707-716; and Embretson et al., 1993 Proc Natl Acad Sci USA, 90 (1), 357-361). Even in HAART patients, residual amounts of HIV is detected (Bailey et al., 2006 J Virol, 80 (13), 6441-6457). Therefore, characterization of these cells provides insight on the mechanism of viral persistence. At first, CD4$^+$ T cells, CD14$^+$ monocytes, and lymphoid tissue from actively infected patients, HAART patients, and elite controllers, who are people that control the HIV infection without HAART, are tested.
Identification of Latently Infected Cells with RT-PCR and Microengraving A single-cell assay for identifying latently infected cells is developed (FIG. 6). Cells are grown in a cocktail of antiretroviral drugs for a few days to allow the unintegrated HIV proviral DNA to decay (Monie et al., 2005 J Virol, 79 (8), 5185-5202). Microengraving is used to identify which cells initially are active producers by detecting viral peptides (e.g., p24, env, gp120, gp41, or p17), viral fragments, or whole virions. Then, the cells are stimulated in the PDMS device and allowed to produce new virus followed by a second printing step, wherein microengraving is used to identify which cells are active producers after stimulation by detecting viral peptides, viral fragments, or whole virions. The cells that are positive in the second print but not the first print are latently infected. For further verification, single cell RT-PCR is performed on the gag mRNA of each cell.

In viraemic patients, the genetic variation of the latently infected population is constantly growing and new strains are continually archived in latent infections (Persaud et al., 2000 J Clin Invest, 105 (7), 995-1003. Interestingly, discontinuing drug treatments in drug-tolerant patients allows drug-sensitive HIV to relapse within weeks (Deeks et al., 2001 N Engl J Med, 344 (7), 472-480). Genetic data on the evolution of known single-point mutations within a host cell provides useful therapeutic information. The extension of RT-PCR methods allow for single-cell screening of genes.
Attachment of DNA onto a Solid Surface for Quantitative Expression Analysis or Sequencing For DNA sequencing to be correlative with the other data gathered about a cell of interest, the amplified DNA sequences must be locally constrained. Several sequencing technologies exist for DNA strands adhered to glass slides and beads (Leamon et al., 2003 Electrophoresis, 24 (21), 3769-3777; Margulies et al., 2005 Nature, 437 (7057), 376-380; and Zhang et al., 2006 Nat Biotechnol, 24 (6), 680-686). One method to attach DNA to the surface is to use primers with a specific sequence at the 5' end (Diehl et al., 2006 Nat Methods, 3 (7), 551-559; Meijer et al., 2006 J Mol Biol, 358 (3), 764-772). This 5' sequence is complementary to a linker sequence provided in the reaction mixture. When this linker sequence also contains a 5' biotin molecule, the oligonucleotide is bound to a streptavidin-coated surface. As a result, amplified target DNA is bound to a surface. In addition, linkers are designed to bring two distant regions together as a method to piece together exons of a gene (Wang, X. and Stollar, B. D., 2000 J Immunol Methods, 244 (1-2), 2 17-225; Meijer et al., 2006 J Mol Biol, 358 (3), 764-772; Embleton et al., 1992 Nucleic Acids Res, 20 (15), 383 1-3837). Since surface attachment depends on the complete lysis of the cell, partially lysed cells could disrupt attachment. In this case, the amplified sequences are constrained to within the cell and not bind to the surface. A possible solution is to use a harsher lysis step to break open the cell membrane.

Surface Capture of mRNA

Figure 5:
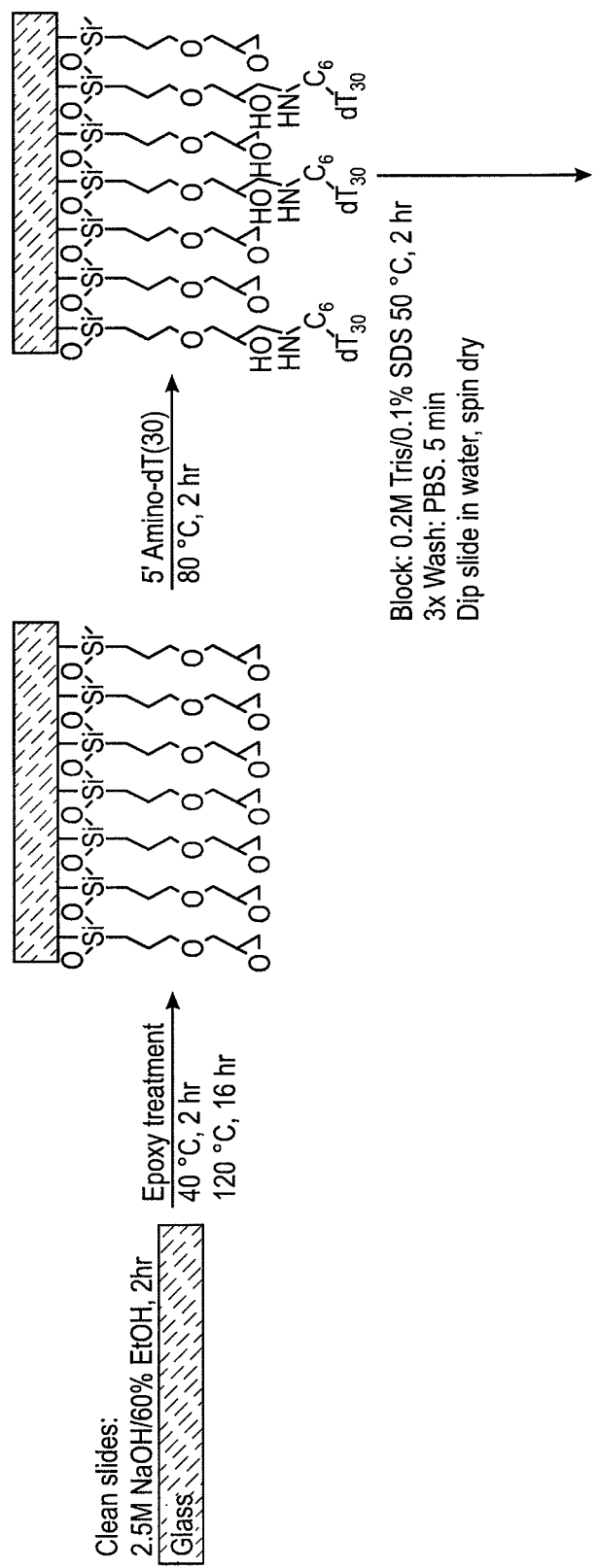
FIG. 5 is a schematic illustrating the capture of beta-2-microglobulin (B2M) mRNA on glass. 4D20 cells were deposited into microwells (left). After imaging, a reverse transcription (RT) master mix (1×RT buffer, 0.5% nonyl phenoxypolyethoxylethanol (NP-40), 20U SUPERASE IN™ RNase inhibitor, and deoxynucleoside triphosphates (dNTPs)) was spread onto the microdevice that was sealed with an oligodeoxythymidylic acid (oligo-dT) functionalized glass. The closed device was placed in an incubator held at 50° C. for 8 hours to allow the heat lysis and RT reaction to proceed. The glass slide was then separated from the microdevice, washed, and hybridized with a HEX-labeled oligonucleotide probe to detect B2M complementary DNA (cDNA; right). Every well that had a cell in it also has the corresponding print and every empty well had no print.
Figure 5:
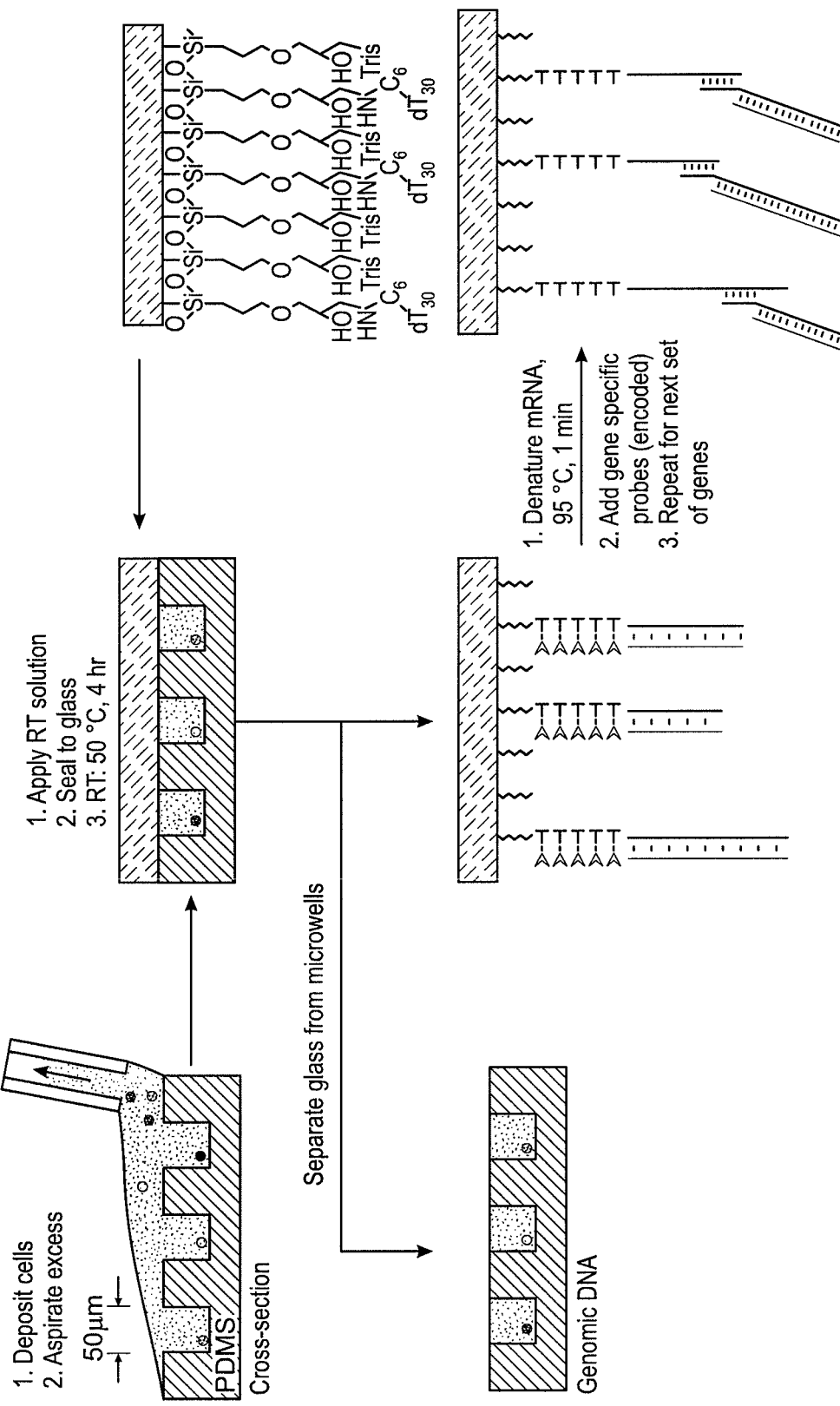
Figure 5:
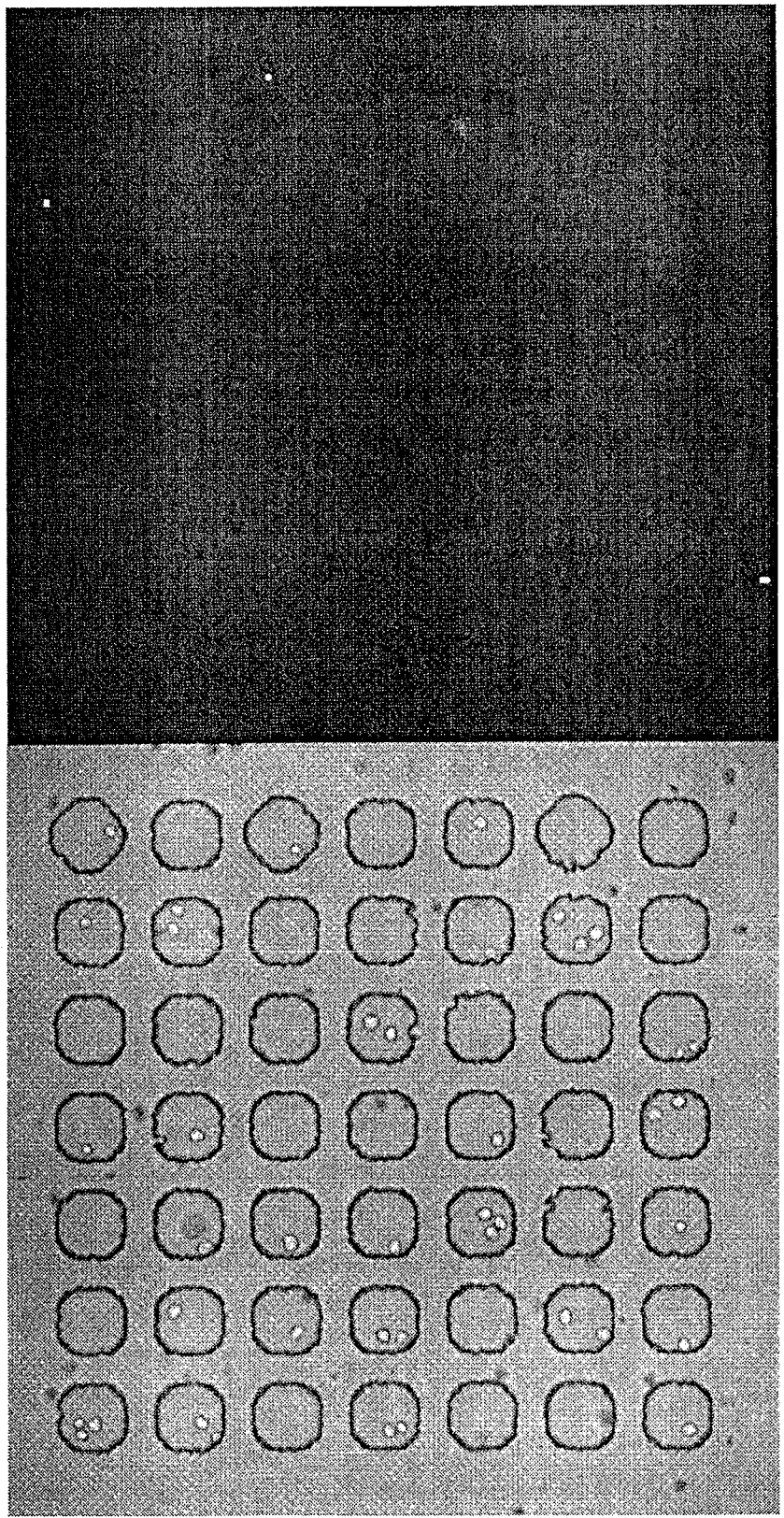

As shown in FIG. 5, beta-2-microglobulin (B2M) mRNA was captured on glass. 4D20 cells were deposited into microwells (FIG. 5, left). After imaging, a reverse transcription (RT) master mix (1×RT buffer, 0.5% nonyl phenoxypolyethoxylethanol (NP-40), 20U SUPERASE IN™ RNase inhibitor, and deoxynucleoside triphosphates (dNTPs)) was spread onto the microdevice that was sealed with an oligodeoxythymidylic acid (oligo-dT) functionalized glass. The closed device was placed in an incubator held at 50° C. for 8 hours to allow the heat lysis and RT reaction to proceed. The glass slide was then separated from the microdevice, washed, and hybridized with a HEX-labeled oligonucleotide probe to detect B2M complementary DNA (cDNA; right). Every well that had a cell in it also has the corresponding print and every empty well had no print.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

---

We claim:

1. A method of performing one-step reverse transcription polymerase chain reaction (RT-PCR) with one cell or a few cells, the method comprising steps of:

sealing a plurality of microwells in a microdevice, wherein each microwell in the plurality contains a subnanoliter volume of liquid, one to three cells and reagents suitable to perform cell lysis and RT-PCR, the sealing forming a substantially fluid-tight seal;

heating the sealed microwells such that cell lysis occurs in the sealed microwells; and subjecting the sealed microwells to thermocycling such that RT-PCR occurs in the microwells, thereby performing one-step RT-PCR with one or a few cells.

2. The method of claim 1, wherein the step of sealing comprises sealing the microwells to a glass slide.

3. The method of claim 1, wherein the reagents comprise a lysis reagent, a reverse transcription reagent, a complementary deoxyribonucleic acid (cDNA) amplification reagent, and primers.

4. The method of claim 1, wherein the reagents comprise detergent, reverse transcriptase, Taq polymerase, and gene-specific probe and primers, wherein the gene specific probe comprises a fluorophore covalently attached to the 5'-end of an oligonucleotide probe and a quencher at the 3'-end of the oligonucleotide probe for real-time PCR quantification.

5. The method of claim 1, wherein the reagents comprise a ribonuclease (RNase) inhibitor.

6. The method of claim 1, wherein the reagents further comprise a reference dye 5-carboxy-X-rhodamine (ROX).

7. The method of claim 1, wherein the microwells are between 10 and 100 μm in diameter.

8. The method of claim 1, wherein the subnanoliter volume is in a range of 1 pL to 500 pL.

9. The method of claim 1, further comprising, before said sealing, a step of culturing the cells in the presence of an anti-retroviral compound, and then depositing the cells in the microwells of the microdevice.

10. The method of claim 9, further comprising, after said depositing and before said sealing, a step of determining by microengraving which cells in the microwells are producing viral peptides, viral fragments, or whole virions;

identifying the cells as virus-producing cells if the cells are determined to be producing viral peptides, viral fragments, or whole virions; and identifying the cells as non-virus-producing cells if the cells are determined not to be producing viral peptides, viral fragments, or whole virions;

wherein the virus is human immunodeficiency virus (HIV), human T cell leukemia virus (HTLV), herpes simplex virus (HSV) 1, HSV 2, or human endogenous retrovirus (Herv).

11. The method of claim 10 wherein the step of determining which cells produce viral peptides, viral fragments, or whole virions comprises performing steps of:

capturing viral peptides, viral fragments, or whole virions produced by the cells on a glass slide functionalized with capture antibody, and probing the glass slide with fluorescently-labeled detection antibody.

12. The method of claim 11, wherein the RT-PCR amplifies an mRNA selected from the group consisting of group-specific antigen (gag) messenger ribonucleic acid (mRNA), polymerase (pol) mRNA, and envelope (env) mRNA.

13. The method of claim 10, wherein the RT-PCR amplifies an mRNA selected from the group consisting of group-specific antigen (gag) messenger ribonucleic acid (mRNA), polymerase (pol) mRNA, and envelope (env) mRNA.

14. The method of claim 1, wherein the cells are immune cells.

15. The method of claim 14, wherein the immune cells are selected from the group consisting of macrophages, monocytes, dendritic cells, and T cells.

16. The method of claim 14, wherein the immune cells are T cells.

17. The method of claim 1, wherein the RT-PCR is performed to amplify an mRNA selected from the group consisting of group-specific antigen (gag) messenger ribonucleic acid (mRNA), polymerase (pol) mRNA, and envelope (env) mRNA.

18. The method of claim 1, wherein the RT-PCR amplifies a viral mRNA.

\* \* \* \* \*

SEQUENCE LISTING

```
<160> NUMBER OF SEQ ID NOS: 16

<210> SEQ ID NO 1
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 1
gaaacccaga cacatagcaa ttcag                                            25

<210> SEQ ID NO 2
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 2
tccagcgtac tccaaagatt cag                                              23

<210> SEQ ID NO 3
<211> LENGTH: 25
<212> TYPE: DNA
<213> ORGANISM: Artificial sequence
<220> FEATURE:
<223> OTHER INFORMATION: Chemically synthesized primer

<400> SEQUENCE: 3
ctcacgtcat ccagcagaga atgga                                            25

<210> SEQ ID NO 4
<211> LENGTH: 24
<212> TYPE: DNA
<213> ORGANISM: Artificial sequence
<220> FEATURE:
<223> OTHER INFORMATION: Chemically synthesized primer

<400> SEQUENCE: 4
gcccctagga aaagggctg ttgg                                              24

<210> SEQ ID NO 5
```

```
<211> LENGTH: 18
<212> TYPE: DNA
<213> ORGANISM: Artificial sequence
<220> FEATURE:
<223> OTHER INFORMATION: Chemically synthesized primer

<400> SEQUENCE: 5
tactgacgct ctcgcacc                                              18

<210> SEQ ID NO 6
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 6
tgaaagattg tactgagaga cagg                                       24

<210> SEQ ID NO 7
<211> LENGTH: 25
<212> TYPE: DNA
<213> ORGANISM: Artificial sequence
<220> FEATURE:
<223> OTHER INFORMATION: Chemically synthesized primer

<400> SEQUENCE: 7
ctcacgtcat ccagcagaga atgga                                      25

<210> SEQ ID NO 8
<211> LENGTH: 21
<212> TYPE: DNA
<213> ORGANISM: Artificial sequence
<220> FEATURE:
<223> OTHER INFORMATION: Chemically synthesized primer

<400> SEQUENCE: 8
ttgccctcaa cgaccacttt g                                          21

<210> SEQ ID NO 9
<211> LENGTH: 18
<212> TYPE: DNA
<213> ORGANISM: Artificial sequence
<220> FEATURE:
<223> OTHER INFORMATION: Chemically synthesized primer

<400> SEQUENCE: 9
gaggtccacc accctgtt                                              18

<210> SEQ ID NO 10
<211> LENGTH: 28
<212> TYPE: DNA
<213> ORGANISM: Artificial sequence
<220> FEATURE:
<223> OTHER INFORMATION: Chemically synthesized primer

<400> SEQUENCE: 10
tcctggtatg acaacgaatt tggctaca                                   28

<210> SEQ ID NO 11
<211> LENGTH: 21
<212> TYPE: DNA
```

```
<213> ORGANISM: Artificial sequence
<220> FEATURE:
<223> OTHER INFORMATION: Chemically synthesized primer

<400> SEQUENCE: 11
gatgcagaag gagatcactg c                                             21

<210> SEQ ID NO 12
<211> LENGTH: 18
<212> TYPE: DNA
<213> ORGANISM: Artificial sequence
<220> FEATURE:
<223> OTHER INFORMATION: Chemically synthesized primer

<400> SEQUENCE: 12
gccgatccac acggagta                                                 18

<210> SEQ ID NO 13
<211> LENGTH: 25
<212> TYPE: DNA
<213> ORGANISM: Artificial sequence
<220> FEATURE:
<223> OTHER INFORMATION: Chemically synthsized primer

<400> SEQUENCE: 13
caagatcatt gctcctcctg agcgc                                         25

<210> SEQ ID NO 14
<211> LENGTH: 19
<212> TYPE: DNA
<213> ORGANISM: Artificial sequence
<220> FEATURE:
<223> OTHER INFORMATION: Chemically synthesized primer

<400> SEQUENCE: 14
ggtcctgtgc tggtgaaac                                                19

<210> SEQ ID NO 15
<211> LENGTH: 22
<212> TYPE: DNA
<213> ORGANISM: Artificial sequence
<220> FEATURE:
<223> OTHER INFORMATION: Chemically synthesized primer

<400> SEQUENCE: 15
gctcacaccc attctatcat tg                                            22

<210> SEQ ID NO 16
<211> LENGTH: 23
<212> TYPE: DNA
<213> ORGANISM: Artificial sequence
<220> FEATURE:
<223> OTHER INFORMATION: Chemically synthesized primer

<400> SEQUENCE: 16
cacagagacc ctcacggtga cct                                           23
```